(12) United States Patent
Globerman et al.

(10) Patent No.: US 9,918,767 B2
(45) Date of Patent: Mar. 20, 2018

(54) TEMPERATURE CONTROL SYSTEM

(75) Inventors: Oren Globerman, Kfar-Shemaryahu (IL); Mordechay Beyar, Caesarea (IL)

(73) Assignee: DePuy Synthes Products, Inc., Raynham, MA (US)

(*) Notice: Subject to any disclaimer, the term of this patent is extended or adjusted under 35 U.S.C. 154(b) by 2457 days.

(21) Appl. No.: 11/561,969

(22) Filed: Nov. 21, 2006

(65) Prior Publication Data

US 2014/0148866 A1  May 29, 2014

Related U.S. Application Data

(63) Continuation-in-part of application No. 11/461,072, filed on Jul. 31, 2006, which is a continuation-in-part of application No. 11/360,251, filed on Feb. 22, 2006, now Pat. No. 8,415,407, application No. 11/561,969, which is a continuation-in-part of application No. PCT/IL2006/000239, filed on Feb. 22, 2006, which is a continuation-in-part of application No. 11/194,411, filed on Aug. 1, 2005.

(60) Provisional application No. 60/814,559, filed on Jun. 19, 2006, provisional application No. 60/765,484, filed on Feb. 2, 2006, provisional application No. (Continued)

(51) Int. Cl.
| | |
|---|---|
| F23N 5/00 | (2006.01) |
| F24F 3/14 | (2006.01) |
| F28F 13/12 | (2006.01) |
| F28F 13/18 | (2006.01) |
| F28F 19/00 | (2006.01) |
| F25B 47/00 | (2006.01) |
| F25D 11/02 | (2006.01) |

| | |
|---|---|
| A61B 17/88 | (2006.01) |
| A61F 2/46 | (2006.01) |

(52) U.S. Cl.
CPC .... A61B 17/8836 (2013.01); A61B 2017/883 (2013.01); A61F 2002/469 (2013.01); A61F 2002/4653 (2013.01)

(58) Field of Classification Search
USPC ............................ 236/46 R; 606/92, 93, 94
See application file for complete search history.

(56) References Cited

U.S. PATENT DOCUMENTS

| | | | |
|---|---|---|---|
| 229,932 | A | 7/1880 | Witsil |
| 370,335 | A | 9/1887 | Hunter |

(Continued)

FOREIGN PATENT DOCUMENTS

| | | |
|---|---|---|
| AU | 724544 | 11/1996 |
| AU | 9865136 | 9/1998 |

(Continued)

OTHER PUBLICATIONS

International Search Report, from corresponding PCT/IL07/01257, dated Jul. 15, 2008.

(Continued)

*Primary Examiner* — Henry Crenshaw
(74) *Attorney, Agent, or Firm* — Nutter McClennen & Fish LLP

(57) ABSTRACT

A method of regulating a setting time of a bone filler material, the method comprising: (a) combining at least two filler material components to form a biocompatible mixture; (b) choosing a setting time for the mixture; and (c) regulating a temperature of the mixture to influence reaction kinetics so that the mixture does not set before the chosen setting time.

20 Claims, 6 Drawing Sheets

Related U.S. Application Data

60/762,789, filed on Jan. 26, 2006, provisional application No. 60/738,556, filed on Nov. 22, 2005.

(56) References Cited

U.S. PATENT DOCUMENTS

| | | |
|---|---|---|
| 408,668 A | 8/1889 | Peck |
| 817,973 A | 4/1906 | Hausman |
| 833,044 A | 10/1906 | Goodhugh |
| 843,587 A | 2/1907 | DePew |
| 1,175,530 A | 3/1916 | Kirchhoff |
| 1,612,281 A | 12/1926 | Goetz |
| 1,612,996 A | 1/1927 | Waagbo |
| 1,733,516 A | 10/1929 | Jamison |
| 1,894,274 A | 1/1933 | Jacques |
| 1,929,247 A | 10/1933 | Hein |
| 2,067,458 A | 1/1937 | Nichols |
| 2,123,712 A | 7/1938 | Clark |
| 2,283,915 A | 5/1942 | Cole |
| 2,394,488 A | 2/1946 | Rotter et al. |
| 2,425,867 A | 8/1947 | Davis |
| 2,435,647 A | 2/1948 | Engseth |
| 2,497,762 A | 2/1950 | Davis |
| 2,521,569 A | 9/1950 | Davis |
| 2,567,960 A | 9/1951 | Meyers et al. |
| 2,745,575 A | 5/1956 | Spencer |
| 2,773,500 A | 12/1956 | Young |
| 2,808,239 A | 10/1957 | Alfred |
| 2,874,877 A | 2/1959 | Spencer |
| 2,918,841 A | 12/1959 | Poupitch |
| 2,928,574 A | 3/1960 | Wagner |
| 2,970,773 A | 2/1961 | Horace et al. |
| 3,058,413 A | 10/1962 | Cavalieri |
| 3,063,449 A | 11/1962 | Schultz |
| 3,075,746 A | 1/1963 | Yablonski et al. |
| 3,108,593 A | 10/1963 | Glassman |
| 3,151,847 A | 10/1964 | Broomall |
| 3,198,194 A | 8/1965 | Wilburn |
| 3,216,616 A | 11/1965 | Blankenship, Jr. |
| 3,224,744 A | 12/1965 | Broomall |
| 3,225,760 A | 12/1965 | Di Cosola |
| 3,254,494 A | 6/1966 | Chartouni |
| 3,362,793 A | 1/1968 | Massoubre |
| 3,381,566 A | 5/1968 | Passer |
| 3,426,364 A | 2/1969 | Lumb |
| 3,515,873 A | 6/1970 | Higgins |
| 3,559,956 A | 2/1971 | Gray |
| 3,568,885 A | 3/1971 | Spencer |
| 3,572,556 A | 3/1971 | Pogacar |
| 3,605,745 A | 9/1971 | Hodosh |
| 3,615,240 A | 10/1971 | Sanz |
| 3,674,011 A | 7/1972 | Michel et al. |
| 3,701,350 A | 10/1972 | Guenther |
| 3,750,667 A | 8/1973 | Pshenichny et al. |
| 3,789,727 A | 2/1974 | Moran |
| 3,796,303 A | 3/1974 | Abbel-Coche |
| 3,798,982 A | 3/1974 | Lundquist |
| 3,846,846 A | 11/1974 | Fischer |
| 3,850,158 A | 11/1974 | Elias et al. |
| 3,867,728 A | 2/1975 | Stubstad et al. |
| 3,873,008 A | 3/1975 | Jahn |
| 3,875,595 A | 4/1975 | Froning |
| 3,896,504 A | 7/1975 | Fischer |
| 3,901,408 A | 8/1975 | Boden et al. |
| 3,921,858 A | 11/1975 | Bemm |
| 3,931,914 A | 1/1976 | Hosaka et al. |
| 3,942,407 A | 3/1976 | Mortensen |
| 3,976,060 A | 8/1976 | Hildebrandt et al. |
| 3,993,250 A | 11/1976 | Shure |
| 4,011,602 A | 3/1977 | Rybicki et al. |
| 4,062,274 A * | 12/1977 | Knab ............................. 454/65 |
| 4,077,494 A | 3/1978 | Spaude et al. |
| 4,079,917 A | 3/1978 | Popeil |
| 4,090,640 A | 5/1978 | Smith et al. |
| 4,093,576 A | 6/1978 | Dewijn Joost |
| 4,105,145 A | 8/1978 | Capra |
| 4,115,346 A | 9/1978 | Gross et al. |
| 4,146,334 A | 3/1979 | Farrell |
| 4,168,787 A | 9/1979 | Stamper |
| 4,170,990 A | 10/1979 | Baumgart et al. |
| 4,180,070 A | 12/1979 | Genese |
| 4,185,072 A | 1/1980 | Puderbaugh et al. |
| 4,189,065 A | 2/1980 | Herold |
| 4,198,383 A | 4/1980 | Konsetov et al. |
| 4,198,975 A | 4/1980 | Haller |
| 4,204,531 A | 5/1980 | Aginsky |
| 4,239,113 A | 12/1980 | Gross et al. |
| 4,250,887 A | 2/1981 | Dardik et al. |
| 4,257,540 A | 3/1981 | Wegmann et al. |
| 4,268,639 A | 5/1981 | Seidel et al. |
| 4,274,163 A | 6/1981 | Malcom et al. |
| 4,276,878 A | 7/1981 | Storz |
| 4,277,184 A | 7/1981 | Solomon |
| 4,298,144 A | 11/1981 | Pressi |
| 4,309,777 A | 1/1982 | Patil |
| 4,312,343 A | 1/1982 | LaVeen et al. |
| 4,313,434 A | 2/1982 | Segal |
| 4,326,567 A | 4/1982 | Mistarz |
| 4,338,925 A | 7/1982 | Miller |
| 4,341,691 A | 7/1982 | Anuta |
| 4,346,708 A | 8/1982 | LeVeen et al. |
| 4,349,921 A | 9/1982 | Kuntz |
| 4,359,049 A | 11/1982 | Redl et al. |
| 4,373,217 A | 2/1983 | Draenert |
| 4,380,398 A | 4/1983 | Burgess |
| 4,400,170 A | 8/1983 | McNaughton et al. |
| 4,403,989 A | 9/1983 | Christensen et al. |
| 4,404,327 A | 9/1983 | Crugnola et al. |
| 4,405,249 A | 9/1983 | Scales |
| 4,409,966 A | 10/1983 | Lambrecht et al. |
| 4,453,539 A | 6/1984 | Raftopoulos et al. |
| 4,474,572 A | 10/1984 | McNaughton et al. |
| 4,475,856 A | 10/1984 | Toomingas |
| 4,476,866 A | 10/1984 | Chin |
| 4,487,602 A | 12/1984 | Christensen et al. |
| 4,494,535 A | 1/1985 | Haig |
| 4,500,658 A | 2/1985 | Fox |
| 4,503,169 A | 3/1985 | Randklev |
| 4,522,200 A | 6/1985 | Stednitz |
| D279,499 S | 7/1985 | Case |
| 4,543,966 A | 10/1985 | Islam et al. |
| 4,546,767 A | 10/1985 | Smith |
| 4,554,914 A | 11/1985 | Kapp et al. |
| 4,558,693 A | 12/1985 | Lash et al. |
| 4,562,598 A | 1/1986 | Kranz |
| 4,576,152 A | 3/1986 | Miller et al. |
| 4,588,583 A | 5/1986 | Pietsch et al. |
| 4,593,685 A | 6/1986 | McKay et al. |
| 4,595,006 A | 6/1986 | Burke et al. |
| 4,600,118 A | 7/1986 | Martin |
| 4,605,011 A | 8/1986 | Naslund |
| 4,632,101 A | 12/1986 | Freedland |
| 4,636,217 A | 1/1987 | Ogilvie et al. |
| 4,642,099 A | 2/1987 | Phillips et al. |
| 4,650,469 A | 3/1987 | Berg et al. |
| 4,651,904 A | 3/1987 | Schuckman |
| 4,653,487 A | 3/1987 | Maale |
| 4,653,489 A | 3/1987 | Tronzo et al. |
| 4,664,298 A | 5/1987 | Shew |
| 4,664,655 A | 5/1987 | Orentreich et al. |
| 4,668,220 A | 5/1987 | Hawrylenko |
| 4,668,295 A | 5/1987 | Abjpai |
| 4,670,008 A | 6/1987 | Von Albertini |
| 4,671,263 A | 6/1987 | Draenert |
| 4,676,655 A | 6/1987 | Handler |
| 4,676,781 A | 6/1987 | Phillips et al. |
| 4,686,973 A | 8/1987 | Frisch |
| 4,697,584 A | 10/1987 | Haynes |
| 4,697,929 A | 10/1987 | Muller |
| 4,704,035 A | 11/1987 | Kowalczyk |
| 4,710,179 A | 12/1987 | Haber et al. |
| 4,714,721 A | 12/1987 | Franek et al. |
| 4,717,383 A | 1/1988 | Phillips et al. |
| 4,718,910 A | 1/1988 | Draenert |
| 4,722,948 A | 2/1988 | Sanderson |

(56) References Cited

U.S. PATENT DOCUMENTS

| | | |
|---|---|---|
| 4,735,616 A | 4/1988 | Eibl et al. |
| 4,737,151 A | 4/1988 | Clement et al. |
| 4,747,832 A | 5/1988 | Buffet |
| 4,758,096 A * | 7/1988 | Gunnarsson ................ 366/139 |
| 4,758,234 A | 7/1988 | Orentreich et al. |
| 4,759,769 A | 7/1988 | Hedman et al. |
| 4,762,515 A | 8/1988 | Grimm |
| 4,767,033 A | 8/1988 | Gemperle |
| 4,772,287 A | 9/1988 | Ray et al. |
| 4,782,118 A | 11/1988 | Fontanille et al. |
| 4,786,184 A | 11/1988 | Berezkina et al. |
| 4,791,150 A | 12/1988 | Braden et al. |
| 4,792,577 A | 12/1988 | Chen et al. |
| 4,804,023 A | 2/1989 | Frearson |
| 4,813,870 A | 3/1989 | Pitzen |
| 4,815,454 A | 3/1989 | Dozier |
| 4,815,632 A | 3/1989 | Ball et al. |
| 4,826,053 A | 5/1989 | Keller |
| 4,830,227 A | 5/1989 | Ball et al. |
| 4,837,279 A | 6/1989 | Arroyo |
| 4,854,312 A | 8/1989 | Raftopoulos et al. |
| 4,854,482 A | 8/1989 | Bergner |
| 4,854,716 A * | 8/1989 | Ziemann et al. ............. 366/139 |
| 4,863,072 A | 9/1989 | Perler |
| 4,869,906 A | 9/1989 | Dingeldein et al. |
| 4,872,936 A | 10/1989 | Engelbrecht |
| 4,892,231 A | 1/1990 | Ball |
| 4,892,550 A | 1/1990 | Huebsch |
| 4,973,301 A | 1/1990 | Nissenkorn |
| 4,902,649 A | 2/1990 | Kimura et al. |
| 4,904,260 A | 2/1990 | Ray et al. |
| 4,908,017 A | 3/1990 | Howson et al. |
| 4,910,259 A | 3/1990 | Kindt-Larsen et al. |
| 4,927,866 A | 5/1990 | Purrmann et al. |
| 4,932,969 A | 6/1990 | Frey et al. |
| 4,935,029 A | 6/1990 | Matsutani et al. |
| 4,944,065 A | 7/1990 | Svanberg et al. |
| 4,944,726 A | 7/1990 | Hilal et al. |
| 4,946,077 A | 8/1990 | Olsen |
| 4,946,285 A | 8/1990 | Vennemeyer |
| 4,946,901 A | 8/1990 | Lechner et al. |
| 4,961,647 A | 10/1990 | Coutts et al. |
| 4,966,601 A | 10/1990 | Draenet |
| 4,968,303 A | 11/1990 | Clarke et al. |
| 4,969,888 A | 11/1990 | Scholten et al. |
| 4,973,168 A * | 11/1990 | Chan ........................... 366/139 |
| 4,973,334 A | 11/1990 | Ziemann |
| 4,978,336 A | 12/1990 | Capozzi et al. |
| 4,983,164 A | 1/1991 | Hook et al. |
| 4,994,065 A | 2/1991 | Gibbs et al. |
| 4,995,868 A | 2/1991 | Brazier |
| 5,004,501 A | 4/1991 | Faccioloi et al. |
| 5,006,112 A | 4/1991 | Metzner |
| 5,012,066 A | 4/1991 | Matsutani et al. |
| 5,015,233 A | 5/1991 | McGough et al. |
| 5,018,919 A | 5/1991 | Stephan |
| 5,022,563 A | 6/1991 | Marchito et al. |
| 5,024,232 A | 6/1991 | Smid et al. |
| 5,028,141 A | 7/1991 | Stiegelmann |
| 5,037,473 A | 8/1991 | Antonucci et al. |
| 5,049,157 A | 9/1991 | Mittelmeier et al. |
| 5,051,482 A | 9/1991 | Tepic |
| 5,059,193 A | 10/1991 | Kuslich |
| 5,059,199 A | 10/1991 | Okada et al. |
| 5,061,128 A | 10/1991 | Jahr et al. |
| 5,062,128 A | 10/1991 | Jahr et al. |
| 5,071,040 A | 12/1991 | Laptewicz, Jr. |
| 5,074,871 A | 12/1991 | Groshong |
| 5,078,919 A | 1/1992 | Ashley et al. |
| 5,092,888 A | 3/1992 | Iwamoto et al. |
| 5,102,413 A | 4/1992 | Poddar |
| 5,108,403 A | 4/1992 | Stern |
| 5,108,404 A | 4/1992 | Scholten et al. |
| 5,112,333 A | 5/1992 | Fixel |
| 5,114,240 A | 5/1992 | Kindt-Larsen et al. |
| 5,116,335 A | 5/1992 | Hannon |
| 5,122,400 A | 6/1992 | Stewart |
| 5,123,926 A | 6/1992 | Pisharodi |
| 5,125,971 A | 6/1992 | Nonami et al. |
| 5,131,382 A | 7/1992 | Meyer |
| 5,141,496 A | 8/1992 | Dalto et al. |
| 5,145,250 A * | 9/1992 | Planck et al. .................... 366/8 |
| 5,147,903 A | 9/1992 | Podszun et al. |
| 5,171,248 A | 12/1992 | Ellis |
| 5,171,278 A | 12/1992 | Pisharodi |
| 5,181,918 A | 1/1993 | Brandhorst et al. |
| 5,188,259 A | 2/1993 | Petit |
| 5,190,191 A | 3/1993 | Reyman |
| 5,192,327 A | 3/1993 | Brantigan |
| 5,193,907 A | 3/1993 | Facciolli |
| 5,203,773 A | 4/1993 | Green |
| 5,209,753 A | 5/1993 | Biedermann et al. |
| 5,217,147 A | 6/1993 | Kaufman |
| 5,219,897 A | 6/1993 | Murray |
| 5,236,445 A | 8/1993 | Hayhurst et al. |
| 5,242,983 A | 9/1993 | Kennedy et al. |
| 5,252,301 A | 10/1993 | Nilson et al. |
| 5,254,092 A | 10/1993 | Polyak |
| 5,258,420 A | 11/1993 | Posey-Dowty et al. |
| 5,264,215 A | 11/1993 | Nakabayashi et al. |
| 5,268,001 A | 12/1993 | Nicholson et al. |
| 5,269,762 A | 12/1993 | Armbruster et al. |
| 5,275,214 A | 1/1994 | Rehberger |
| 5,276,070 A | 1/1994 | Arroyo |
| 5,277,339 A | 1/1994 | Shew et al. |
| 5,279,555 A | 1/1994 | Lifshey |
| 5,290,260 A | 3/1994 | Stines |
| 5,295,980 A | 3/1994 | Ersek |
| 5,302,020 A | 4/1994 | Kruse |
| 5,303,718 A | 4/1994 | Kajicek |
| 5,304,147 A | 4/1994 | Johnson et al. |
| 5,318,532 A | 6/1994 | Frassica |
| 5,328,262 A | 7/1994 | Lidgren et al. |
| 5,328,362 A | 7/1994 | Watson et al. |
| 5,331,972 A | 7/1994 | Wadhwani et al. |
| 5,333,951 A | 8/1994 | Wakoh |
| 5,334,184 A | 8/1994 | Bimman |
| 5,334,626 A | 8/1994 | Lin |
| 5,336,699 A | 8/1994 | Cooke et al. |
| 5,336,700 A | 8/1994 | Murray |
| 5,344,232 A | 9/1994 | Nelson et al. |
| 5,348,391 A | 9/1994 | Murray |
| 5,348,548 A | 9/1994 | Meyer et al. |
| 5,350,372 A | 9/1994 | Ikeda et al. |
| 5,354,287 A | 10/1994 | Wacks |
| 5,356,382 A | 10/1994 | Picha et al. |
| 5,368,046 A | 11/1994 | Scarfone et al. |
| 5,368,386 A | 11/1994 | Murray |
| 5,370,221 A | 12/1994 | Magnusson et al. |
| 5,372,583 A | 12/1994 | Roberts et al. |
| 5,374,427 A | 12/1994 | Stille et al. |
| 5,375,583 A | 12/1994 | Roberts |
| 5,376,123 A | 12/1994 | Klaue et al. |
| 5,380,772 A | 1/1995 | Hasegawa et al. |
| 5,385,081 A | 1/1995 | Sneddon |
| 5,385,566 A | 1/1995 | Ullmaerk |
| 5,387,191 A | 2/1995 | Hemstreet et al. |
| 5,390,683 A | 2/1995 | Pisharodi |
| 5,395,167 A | 3/1995 | Murray |
| 5,395,326 A | 3/1995 | Haber et al. |
| 5,398,483 A | 3/1995 | Smith et al. |
| 5,401,806 A | 3/1995 | Braden et al. |
| 5,407,266 A | 4/1995 | Dotsch et al. |
| 5,411,180 A | 5/1995 | Dumelle |
| 5,415,474 A | 5/1995 | Nelson et al. |
| 5,423,824 A | 6/1995 | Akerfeldt et al. |
| 5,423,850 A | 6/1995 | Berger |
| 5,431,654 A | 7/1995 | Nic |
| 5,435,645 A | 7/1995 | Faccioli |
| 5,441,502 A | 8/1995 | Bartlett |
| 5,443,182 A | 8/1995 | Tanaka et al. |
| 5,445,639 A | 8/1995 | Kuslich et al. |
| 5,450,924 A | 9/1995 | Tseng |
| 5,454,365 A | 10/1995 | Bonutti |

(56) References Cited

U.S. PATENT DOCUMENTS

| | | |
|---|---|---|
| 5,456,267 A | 10/1995 | Stark |
| 5,468,245 A | 11/1995 | Vargas, III |
| 5,480,400 A | 1/1996 | Berger |
| 5,480,403 A | 1/1996 | Lee |
| 5,482,187 A | 1/1996 | Poulsen et al. |
| 5,492,247 A | 2/1996 | Shu et al. |
| 5,494,349 A | 2/1996 | Seddon |
| 5,501,374 A | 3/1996 | Laufer et al. |
| 5,501,520 A | 3/1996 | Lidgren et al. |
| 5,501,695 A | 3/1996 | Anspach, Jr. et al. |
| 5,512,610 A | 4/1996 | Lin |
| 5,514,135 A | 5/1996 | Earle |
| 5,514,137 A | 5/1996 | Coutts |
| 5,518,498 A | 5/1996 | Lindenberg et al. |
| 5,520,690 A | 5/1996 | Errico et al. |
| 5,522,816 A | 6/1996 | Dinello et al. |
| 5,522,899 A | 6/1996 | Michelson |
| 5,526,853 A | 6/1996 | McPhee et al. |
| 5,531,519 A * | 7/1996 | Earle .................... 366/139 |
| 5,531,683 A | 7/1996 | Kriesel et al. |
| 5,534,028 A | 7/1996 | Bao et al. |
| 5,536,262 A | 7/1996 | Velasquez |
| 5,545,460 A | 8/1996 | Tanaka et al. |
| 5,548,001 A | 8/1996 | Podszun et al. |
| 5,549,380 A | 8/1996 | Lidgren et al. |
| 5,549,381 A | 8/1996 | Hays et al. |
| 5,549,679 A | 8/1996 | Kuslich |
| 5,551,778 A | 9/1996 | Hauke et al. |
| 5,554,101 A | 9/1996 | Matula et al. |
| 5,556,201 A | 9/1996 | Veltrop et al. |
| 5,558,136 A | 9/1996 | Orrico |
| 5,558,639 A | 9/1996 | Gangemi et al. |
| 5,571,189 A | 11/1996 | Kuslich et al. |
| 5,573,265 A | 11/1996 | Pradel |
| 5,578,035 A | 11/1996 | Lin |
| 5,586,821 A | 12/1996 | Bonitati et al. |
| 5,588,745 A | 12/1996 | Tanaka et al. |
| 5,591,197 A | 1/1997 | Orth et al. |
| 5,601,557 A | 2/1997 | Hayhurst |
| 5,603,701 A | 2/1997 | Fisher |
| 5,609,637 A | 3/1997 | Biedermann et al. |
| 5,624,184 A | 4/1997 | Chan |
| 5,630,806 A | 5/1997 | Inagaki et al. |
| 5,634,880 A | 6/1997 | Feldman et al. |
| 5,637,097 A | 6/1997 | Yoon |
| 5,638,997 A | 6/1997 | Hawkins et al. |
| 5,641,010 A | 6/1997 | Maier |
| 5,645,598 A | 7/1997 | Brosnahan, III |
| 5,647,856 A | 7/1997 | Eykmann |
| 5,653,686 A | 8/1997 | Coulter et al. |
| 5,658,310 A | 8/1997 | Berger |
| 5,660,186 A | 8/1997 | Bachir |
| 5,665,067 A | 9/1997 | Linder et al. |
| 5,681,317 A | 10/1997 | Caldarise |
| 5,683,451 A | 11/1997 | Lenker et al. |
| 5,685,826 A | 11/1997 | Bonutti |
| 5,690,606 A | 11/1997 | Slotman |
| 5,693,100 A | 12/1997 | Pisharodi |
| 5,697,977 A | 12/1997 | Pisharodi |
| 5,698,611 A | 12/1997 | Okada et al. |
| 5,702,448 A | 12/1997 | Buechel et al. |
| 5,704,895 A | 1/1998 | Scott et al. |
| 5,707,390 A | 1/1998 | Bonutti |
| 5,718,707 A | 2/1998 | Mikhail |
| 5,720,753 A | 2/1998 | Sander et al. |
| 5,725,341 A | 3/1998 | Hofmeister |
| 5,725,529 A | 3/1998 | Nicholson et al. |
| 5,747,553 A | 5/1998 | Guzauskas |
| 5,752,935 A | 5/1998 | Robinson et al. |
| 5,752,969 A | 5/1998 | Cunci et al. |
| 5,752,974 A | 5/1998 | Rhee |
| 5,755,732 A | 5/1998 | Green et al. |
| 5,759,186 A | 6/1998 | Bachmann et al. |
| 5,763,092 A | 6/1998 | Lee et al. |
| 5,779,356 A | 7/1998 | Chan |
| 5,782,713 A | 7/1998 | Yang |
| 5,782,747 A | 7/1998 | Zimmon |
| 5,782,830 A | 7/1998 | Farris |
| 5,782,838 A | 7/1998 | Beyar et al. |
| 5,785,647 A | 7/1998 | Tompkins et al. |
| 5,785,682 A | 7/1998 | Grabenkort |
| 5,792,044 A | 8/1998 | Foley |
| 5,795,922 A | 8/1998 | Demian et al. |
| 5,797,678 A * | 8/1998 | Murray .................... 366/139 |
| 5,800,169 A | 9/1998 | Muhlbauer |
| 5,800,409 A | 9/1998 | Bruce |
| 5,800,549 A | 9/1998 | Bao et al. |
| 5,800,550 A | 9/1998 | Sertich |
| 5,820,321 A | 10/1998 | Gruber |
| 5,824,087 A | 10/1998 | Aspden et al. |
| 5,826,713 A | 10/1998 | Sunago et al. |
| 5,826,753 A | 10/1998 | Fehlig et al. |
| 5,827,217 A | 10/1998 | Silver et al. |
| 5,827,289 A | 10/1998 | Reiley et al. |
| 5,829,875 A | 11/1998 | Hagel et al. |
| 5,830,194 A | 11/1998 | Anwar et al. |
| 5,836,306 A | 11/1998 | Duane et al. |
| 5,839,621 A | 11/1998 | Tada |
| 5,842,785 A | 12/1998 | Brown et al. |
| 5,865,802 A | 2/1999 | Yoon et al. |
| 5,876,116 A | 3/1999 | Barker et al. |
| 5,876,457 A | 3/1999 | Picha et al. |
| 5,882,340 A | 3/1999 | Yoon et al. |
| 5,884,818 A | 3/1999 | Campbell |
| 5,893,488 A | 4/1999 | Hoag et al. |
| 5,893,850 A | 4/1999 | Cachia |
| 5,902,839 A | 5/1999 | Lautenschlager et al. |
| 5,911,721 A | 6/1999 | Nicholson et al. |
| 5,918,702 A | 7/1999 | Cheng et al. |
| 5,918,770 A | 7/1999 | Camm et al. |
| 5,925,051 A | 7/1999 | Mikhail |
| 5,928,239 A | 7/1999 | Mirza |
| 5,931,347 A | 8/1999 | Haubrich |
| 5,941,851 A | 8/1999 | Coffey et al. |
| 5,954,671 A | 9/1999 | O'Neill |
| 5,954,728 A | 9/1999 | Heller et al. |
| 5,961,211 A | 10/1999 | Barker et al. |
| 5,968,008 A | 10/1999 | Grams |
| 5,968,044 A | 10/1999 | Nicholson et al. |
| 5,968,999 A | 10/1999 | Ramp et al. |
| 5,972,015 A | 10/1999 | Scribner et al. |
| 5,980,527 A | 11/1999 | Cohen et al. |
| 5,993,535 A | 11/1999 | Sawamura et al. |
| 5,997,544 A | 12/1999 | Nies et al. |
| 6,004,325 A | 12/1999 | Vargas, III |
| 6,007,496 A | 12/1999 | Brannon |
| 6,017,349 A | 1/2000 | Heller et al. |
| 6,019,765 A | 2/2000 | Thornhill et al. |
| 6,019,776 A | 2/2000 | Preissman et al. |
| 6,019,789 A | 2/2000 | Dinh et al. |
| 6,020,396 A | 2/2000 | Jacobs |
| 6,022,339 A | 2/2000 | Fowles et al. |
| 6,033,105 A | 3/2000 | Barker et al. |
| 6,033,411 A | 3/2000 | Preissman |
| 6,039,761 A | 3/2000 | Li et al. |
| 6,040,408 A | 3/2000 | Koole |
| 6,041,977 A | 3/2000 | Lisi |
| 6,042,262 A | 3/2000 | Hajianpour |
| 6,045,555 A | 4/2000 | Smith et al. |
| 6,048,346 A | 4/2000 | Reiley |
| 6,049,026 A | 4/2000 | Muschler |
| 6,075,067 A * | 6/2000 | Lidgren .................... 523/116 |
| 6,080,579 A | 6/2000 | Hanley, Jr. |
| 6,080,801 A | 6/2000 | Draenert et al. |
| 6,080,811 A | 6/2000 | Schehlmann et al. |
| 6,083,229 A | 7/2000 | Constantz et al. |
| 6,086,594 A | 7/2000 | Brown |
| 6,103,779 A | 8/2000 | Guzauskas |
| 6,116,773 A | 9/2000 | Murray |
| 6,120,174 A | 9/2000 | Hoag et al. |
| 6,124,373 A | 9/2000 | Peter et al. |
| 6,126,689 A | 10/2000 | Brett |
| 6,127,597 A | 10/2000 | Beyar et al. |
| 6,129,763 A | 10/2000 | Chauvin et al. |

(56) References Cited

U.S. PATENT DOCUMENTS

| | | |
|---|---|---|
| 6,132,396 A | 10/2000 | Antanavich et al. |
| 6,136,038 A | 10/2000 | Raab |
| 6,139,509 A | 10/2000 | Yuan et al. |
| 6,142,998 A | 11/2000 | Smith et al. |
| 6,146,401 A | 11/2000 | Yoon et al. |
| 6,149,651 A | 11/2000 | Drewry et al. |
| 6,149,655 A | 11/2000 | Constantz et al. |
| 6,149,664 A | 11/2000 | Kurz |
| 6,160,033 A | 12/2000 | Nies |
| 6,161,955 A | 12/2000 | Rademaker |
| 6,168,597 B1 | 1/2001 | Biedermann et al. |
| 6,174,935 B1 | 1/2001 | Matsunae et al. |
| 6,176,607 B1 | 1/2001 | Hajianpour |
| 6,183,441 B1 | 2/2001 | Kriesel et al. |
| 6,183,516 B1 | 2/2001 | Burkinshaw et al. |
| 6,187,015 B1 | 2/2001 | Brenneman |
| 6,190,381 B1 | 2/2001 | Olsen et al. |
| 6,206,058 B1 | 3/2001 | Nagel et al. |
| 6,221,029 B1 | 3/2001 | Mathis et al. |
| 6,210,031 B1 | 4/2001 | Murray |
| 6,214,012 B1 | 4/2001 | Karpman et al. |
| 6,214,016 B1 | 4/2001 | Williams et al. |
| 6,214,037 B1 | 4/2001 | Mitchell et al. |
| 6,217,566 B1 | 4/2001 | Ju et al. |
| 6,217,581 B1 | 4/2001 | Tolson |
| 6,217,608 B1 | 4/2001 | Penn et al. |
| 6,224,604 B1 | 5/2001 | Suddaby |
| 6,228,049 B1 | 5/2001 | Schroeder et al. |
| 6,228,068 B1 | 5/2001 | Yoon |
| 6,228,082 B1 | 5/2001 | Baker et al. |
| 6,231,615 B1 | 5/2001 | Preissman |
| 6,235,043 B1 | 5/2001 | Reiley et al. |
| 6,238,399 B1 | 5/2001 | Heller et al. |
| 6,241,734 B1 | 6/2001 | Scribner et al. |
| 6,245,101 B1 | 6/2001 | Drasler et al. |
| 6,248,110 B1 | 6/2001 | Reiley et al. |
| 6,254,268 B1 * | 7/2001 | Long .............. 366/139 |
| 6,261,289 B1 | 7/2001 | Levy |
| 6,264,618 B1 | 7/2001 | Landi et al. |
| 6,264,659 B1 | 7/2001 | Ross et al. |
| 6,264,660 B1 | 7/2001 | Schmidt et al. |
| 6,273,916 B1 | 8/2001 | Murphy |
| 6,281,271 B1 | 8/2001 | Rumphorst et al. |
| 6,309,395 B1 | 10/2001 | Smith et al. |
| 6,309,420 B1 | 10/2001 | Preissman |
| 6,312,149 B1 | 11/2001 | Sojovall et al. |
| 6,325,812 B1 | 12/2001 | Dubrul et al. |
| 6,348,055 B1 | 2/2002 | Preissman |
| 6,348,518 B1 | 2/2002 | Montgomery |
| 6,350,271 B1 | 2/2002 | Kurz et al. |
| 6,361,539 B1 | 3/2002 | Heller et al. |
| 6,364,865 B1 | 4/2002 | Lavi et al. |
| 6,367,962 B1 | 4/2002 | Mizutani et al. |
| 6,375,659 B1 | 4/2002 | Erbe et al. |
| 6,375,682 B1 | 4/2002 | Fleischmann et al. |
| 6,383,188 B2 | 5/2002 | Kuslich et al. |
| 6,383,190 B1 | 5/2002 | Preissman |
| 6,395,007 B1 | 5/2002 | Bhatnagar |
| 6,402,701 B1 | 6/2002 | Kaplan et al. |
| 6,402,758 B1 | 6/2002 | Tolson |
| 6,406,175 B1 * | 6/2002 | Marino .............. 366/130 |
| 6,409,972 B1 | 6/2002 | Chan |
| 6,410,612 B1 | 6/2002 | Hatanaka |
| 6,425,885 B1 | 7/2002 | Fischer et al. |
| 6,425,887 B1 | 7/2002 | McGuckin et al. |
| 6,431,743 B1 | 8/2002 | Mizutani et al. |
| 6,433,037 B1 | 8/2002 | Guzauskas |
| 6,436,143 B1 | 8/2002 | Ross et al. |
| 6,439,439 B1 | 8/2002 | Rickard |
| 6,443,334 B1 | 9/2002 | John et al. |
| 6,447,478 B1 | 9/2002 | Maynards |
| 6,450,973 B1 | 9/2002 | Murphy |
| 6,458,117 B1 | 10/2002 | Pollins, Sr. |
| 6,479,565 B1 | 11/2002 | Stanley |
| 6,488,667 B1 | 12/2002 | Murphy |
| 6,494,868 B2 | 12/2002 | Amar |
| 6,500,182 B2 | 12/2002 | Foster |
| 6,502,608 B1 | 1/2003 | Burchett et al. |
| 6,527,144 B2 | 3/2003 | Ritsche et al. |
| 6,550,957 B2 | 4/2003 | Mizutani et al. |
| 6,554,833 B2 | 4/2003 | Levy et al. |
| 6,568,439 B1 | 5/2003 | Se et al. |
| 6,572,256 B2 | 6/2003 | Seaton et al. |
| 6,575,331 B1 | 6/2003 | Peeler et al. |
| 6,575,919 B1 | 6/2003 | Reiley et al. |
| 6,582,439 B1 | 6/2003 | Sproul |
| 6,592,559 B1 | 7/2003 | Pakter et al. |
| 6,595,967 B2 | 7/2003 | Kramer |
| 6,599,293 B2 | 7/2003 | Tague et al. |
| 6,599,520 B2 | 7/2003 | Scarborough et al. |
| 6,613,018 B2 | 9/2003 | Bagga |
| 6,613,054 B2 | 9/2003 | Scribner et al. |
| 6,626,912 B2 | 9/2003 | Speitling |
| 6,641,587 B2 | 11/2003 | Scribner et al. |
| 6,645,213 B2 | 11/2003 | Sand et al. |
| 6,662,969 B2 | 12/2003 | Peeler et al. |
| 6,676,664 B1 | 1/2004 | Al-Assir |
| 6,689,823 B1 | 2/2004 | Bellare et al. |
| 6,702,455 B2 | 3/2004 | Vendrely et al. |
| 6,712,853 B2 | 3/2004 | Kuslich |
| 6,716,216 B1 | 4/2004 | Boucher et al. |
| 6,719,761 B1 | 4/2004 | Reiley et al. |
| 6,720,417 B1 | 4/2004 | Walter |
| 6,730,095 B2 | 5/2004 | Olson, Jr. et al. |
| 6,752,180 B2 | 6/2004 | Delay |
| 6,758,837 B2 | 7/2004 | Peciat et al. |
| 6,759,449 B2 | 7/2004 | Kimura et al. |
| 6,767,973 B2 | 7/2004 | Suau et al. |
| 6,770,079 B2 * | 8/2004 | Bhatnagar et al. ........... 606/94 |
| 6,779,566 B2 | 8/2004 | Engel |
| 6,780,175 B1 | 8/2004 | Sachdeva et al. |
| 6,783,515 B1 | 8/2004 | Miller et al. |
| 6,787,584 B2 | 9/2004 | Jia et al. |
| 6,796,987 B2 | 9/2004 | Tague et al. |
| 6,852,439 B2 | 2/2005 | Frank |
| 6,874,927 B2 | 4/2005 | Foster |
| 6,875,219 B2 | 4/2005 | Arramon et al. |
| 6,887,246 B2 * | 5/2005 | Bhatnagar et al. ........... 606/94 |
| 6,916,308 B2 | 7/2005 | Dixon et al. |
| 6,957,747 B2 | 10/2005 | Peeler et al. |
| 6,974,247 B2 | 12/2005 | Frei et al. |
| 6,974,416 B2 | 12/2005 | Booker et al. |
| 6,979,341 B2 | 12/2005 | Scribner et al. |
| 6,979,352 B2 | 12/2005 | Reynolds |
| 6,994,465 B2 | 2/2006 | Tague et al. |
| 6,997,930 B1 | 2/2006 | Jaggi |
| 7,008,433 B2 | 3/2006 | Voellmicke et al. |
| 7,025,771 B2 | 4/2006 | Kuslich et al. |
| 7,029,163 B2 | 4/2006 | Barker et al. |
| 7,044,954 B2 | 5/2006 | Reiley |
| 7,048,743 B2 | 5/2006 | Miller |
| 7,066,942 B2 | 6/2006 | Treace |
| 7,087,040 B2 | 8/2006 | McGuckin |
| 7,091,258 B2 | 8/2006 | Neubert et al. |
| 7,097,648 B1 | 8/2006 | Globerman et al. |
| 7,112,205 B2 | 9/2006 | Carrison |
| 7,116,121 B1 | 10/2006 | Holcombe et al. |
| 7,252,671 B2 | 8/2007 | Scribner |
| 7,264,622 B2 * | 9/2007 | Michelson ............ 606/86 A |
| 7,270,667 B2 | 9/2007 | Faccioli |
| 7,278,778 B2 | 10/2007 | Sand |
| 7,320,540 B2 | 1/2008 | Coffeen |
| 7,326,203 B2 | 2/2008 | Papineau et al. |
| 7,456,024 B2 | 11/2008 | Dahm et al. |
| 7,470,258 B2 | 12/2008 | Barker et al. |
| 7,559,932 B2 | 7/2009 | Truckai et al. |
| 7,572,263 B2 | 8/2009 | Preismann |
| 7,604,618 B2 | 10/2009 | Dixon et al. |
| 7,666,205 B2 | 2/2010 | Weikel et al. |
| 7,678,116 B2 | 3/2010 | Truckai et al. |
| 7,717,918 B2 | 5/2010 | Truckai et al. |
| 7,722,620 B2 | 5/2010 | Truckai et al. |
| 8,038,682 B2 | 10/2011 | McGill et al. |
| 8,066,713 B2 | 11/2011 | DiMauro et al. |

(56) References Cited

U.S. PATENT DOCUMENTS

| | | | |
|---|---|---|---|
| 8,070,753 B2 | 12/2011 | Truckai et al. | |
| 8,333,773 B2 | 12/2012 | DiMauro et al. | |
| 8,360,629 B2 | 1/2013 | Globerman et al. | |
| 8,361,078 B2 | 1/2013 | Beyar et al. | |
| 8,415,407 B2 | 4/2013 | Beyar et al. | |
| 8,540,722 B2 | 9/2013 | Beyar et al. | |
| 8,809,418 B2 | 8/2014 | Beyar et al. | |
| 8,950,929 B2 | 2/2015 | Globerman et al. | |
| 8,956,368 B2 | 2/2015 | Beyar et al. | |
| 9,186,194 B2 | 11/2015 | Ferreyro et al. | |
| 9,259,696 B2 | 2/2016 | Globerman et al. | |
| 9,381,024 B2 | 7/2016 | Globerman et al. | |
| 9,504,508 B2 | 11/2016 | Beyar et al. | |
| 9,642,932 B2 | 5/2017 | Beyar et al. | |
| 9,750,840 B2 | 9/2017 | Beyar et al. | |
| 2001/0012968 A1 | 8/2001 | Preissman | |
| 2001/0024400 A1* | 9/2001 | Van Der Wel | 366/143 |
| 2001/0034527 A1 | 10/2001 | Scribner et al. | |
| 2002/0008122 A1 | 1/2002 | Ritsche et al. | |
| 2002/0010471 A1 | 1/2002 | Wironen | |
| 2002/0010472 A1 | 1/2002 | Kuslich et al. | |
| 2002/0013553 A1 | 1/2002 | Pajunk | |
| 2002/0099385 A1 | 1/2002 | Ralph et al. | |
| 2002/0049448 A1 | 4/2002 | Sand et al. | |
| 2002/0049449 A1 | 4/2002 | Bhatnagar et al. | |
| 2002/0058947 A1 | 5/2002 | Hochschuler et al. | |
| 2002/0067658 A1 | 6/2002 | Vendrely et al. | |
| 2002/0068939 A1 | 6/2002 | Levy et al. | |
| 2002/0068974 A1 | 6/2002 | Kuslich et al. | |
| 2002/0068975 A1 | 6/2002 | Teitelbaum et al. | |
| 2002/0072768 A1 | 6/2002 | Ginn | |
| 2002/0082605 A1* | 6/2002 | Reiley et al. | 606/93 |
| 2002/0099384 A1 | 7/2002 | Scribner et al. | |
| 2002/0118595 A1 | 8/2002 | Miller | |
| 2002/0123716 A1 | 9/2002 | VanDiver et al. | |
| 2002/0156483 A1 | 10/2002 | Voellmicke et al. | |
| 2002/0161373 A1 | 10/2002 | Osorio et al. | |
| 2002/0177866 A1 | 11/2002 | Weikel et al. | |
| 2002/0183851 A1* | 12/2002 | Spiegelberg et al. | 623/22.12 |
| 2002/0188300 A1 | 12/2002 | Arramon | |
| 2002/0191487 A1 | 12/2002 | Sand | |
| 2003/0009177 A1 | 1/2003 | Middleman et al. | |
| 2003/0018339 A1 | 1/2003 | Higueras et al. | |
| 2003/0031698 A1 | 2/2003 | Roeder et al. | |
| 2003/0032929 A1 | 2/2003 | McGuckin et al. | |
| 2003/0036763 A1 | 2/2003 | Bhatnager et al. | |
| 2003/0040718 A1 | 2/2003 | Keahey et al. | |
| 2003/0050644 A1 | 3/2003 | Boucher et al. | |
| 2003/0050702 A1 | 3/2003 | Berger | |
| 2003/0078589 A1 | 4/2003 | Preissman | |
| 2003/0109883 A1 | 6/2003 | Matsuzaki et al. | |
| 2003/0109884 A1 | 6/2003 | Tague et al. | |
| 2003/0144742 A1 | 7/2003 | King et al. | |
| 2003/0162864 A1 | 8/2003 | Pearson et al. | |
| 2003/0174576 A1 | 9/2003 | Tague et al. | |
| 2003/0181963 A1 | 9/2003 | Pellegrino et al. | |
| 2003/0185093 A1 | 10/2003 | Vendrely et al. | |
| 2003/0220414 A1 | 11/2003 | Axen et al. | |
| 2003/0225364 A1 | 12/2003 | Kraft et al. | |
| 2003/0227816 A1 | 12/2003 | Okamoto et al. | |
| 2003/0231545 A1 | 12/2003 | Seaton | |
| 2004/0010263 A1 | 1/2004 | Boucher et al. | |
| 2004/0029996 A1 | 2/2004 | Kuhn | |
| 2004/0054377 A1 | 3/2004 | Foster et al. | |
| 2004/0066706 A1* | 4/2004 | Barker et al. | 366/139 |
| 2004/0068264 A1 | 4/2004 | Treace | |
| 2004/0073139 A1 | 4/2004 | Hirsch et al. | |
| 2004/0092946 A1 | 5/2004 | Bagga et al. | |
| 2004/0098015 A1 | 5/2004 | Weikel et al. | |
| 2004/0106913 A1 | 6/2004 | Eidenschink et al. | |
| 2004/0122438 A1 | 6/2004 | Abrams | |
| 2004/0132859 A1 | 7/2004 | Puckett, Jr. et al. | |
| 2004/0133211 A1 | 7/2004 | Raskin et al. | |
| 2004/0138759 A1 | 7/2004 | Muller et al. | |
| 2004/0157952 A1 | 8/2004 | Soffiati et al. | |
| 2004/0157954 A1 | 8/2004 | Imai et al. | |
| 2004/0162559 A1 | 8/2004 | Arramon et al. | |
| 2004/0167532 A1 | 8/2004 | Olson et al. | |
| 2004/0167562 A1 | 8/2004 | Osorio et al. | |
| 2004/0167625 A1 | 8/2004 | Beyar et al. | |
| 2004/0193171 A1* | 9/2004 | DiMauro et al. | 606/92 |
| 2004/0215202 A1 | 10/2004 | Preissman | |
| 2004/0220672 A1 | 11/2004 | Shadduck | |
| 2004/0226479 A1 | 11/2004 | Lyles et al. | |
| 2004/0229972 A1 | 11/2004 | Klee et al. | |
| 2004/0230309 A1 | 11/2004 | DiMauro et al. | |
| 2004/0236313 A1 | 11/2004 | Klein | |
| 2004/0249015 A1 | 12/2004 | Jia et al. | |
| 2004/0249347 A1 | 12/2004 | Miller et al. | |
| 2004/0260303 A1 | 12/2004 | Carrison | |
| 2004/0260304 A1 | 12/2004 | Faccioli et al. | |
| 2004/0267154 A1 | 12/2004 | Sutton et al. | |
| 2005/0014273 A1 | 1/2005 | Dahm | |
| 2005/0015148 A1 | 1/2005 | Jansen et al. | |
| 2005/0025622 A1 | 2/2005 | Djeridane et al. | |
| 2005/0058717 A1 | 3/2005 | Yetlinler | |
| 2005/0060023 A1 | 3/2005 | Mitchell et al. | |
| 2005/0070912 A1 | 3/2005 | Voellmicke | |
| 2005/0070914 A1 | 3/2005 | Constantz et al. | |
| 2005/0070915 A1 | 3/2005 | Mazzuca | |
| 2005/0083782 A1 | 4/2005 | Gronau et al. | |
| 2005/0113762 A1 | 5/2005 | Kay et al. | |
| 2005/0143827 A1 | 6/2005 | Globerman et al. | |
| 2005/0154081 A1 | 7/2005 | Yin et al. | |
| 2005/0159724 A1 | 7/2005 | Enerson | |
| 2005/0180806 A1 | 8/2005 | Green | |
| 2005/0203206 A1 | 9/2005 | Trieu | |
| 2005/0209695 A1 | 9/2005 | de Vries et al. | |
| 2005/0216025 A1 | 9/2005 | Chern Lin et al. | |
| 2005/0256220 A1 | 11/2005 | Lavergne et al. | |
| 2005/0281132 A1 | 12/2005 | Armstrong et al. | |
| 2006/0035997 A1 | 2/2006 | Orlowski et al. | |
| 2006/0041033 A1 | 2/2006 | Bisig et al. | |
| 2006/0052794 A1 | 3/2006 | McGill | |
| 2006/0074433 A1 | 4/2006 | McGill et al. | |
| 2006/0079905 A1 | 4/2006 | Beyar et al. | |
| 2006/0116643 A1 | 6/2006 | Dixon et al. | |
| 2006/0116689 A1 | 6/2006 | Albans et al. | |
| 2006/0116690 A1 | 6/2006 | Pagano | |
| 2006/0122614 A1 | 6/2006 | Truckai et al. | |
| 2006/0148923 A1 | 7/2006 | Ashman et al. | |
| 2006/0167148 A1 | 7/2006 | Engquist et al. | |
| 2006/0181959 A1 | 8/2006 | Weiss et al. | |
| 2006/0235338 A1 | 10/2006 | Pacheco | |
| 2006/0241644 A1 | 10/2006 | Osorio et al. | |
| 2006/0264695 A1 | 11/2006 | Viole et al. | |
| 2006/0264967 A1 | 11/2006 | Ferreyro et al. | |
| 2006/0266372 A1 | 11/2006 | Miller et al. | |
| 2006/0271061 A1 | 11/2006 | Beyar et al. | |
| 2006/0276819 A1 | 12/2006 | Osorio et al. | |
| 2007/0027230 A1 | 2/2007 | Beyar et al. | |
| 2007/0032567 A1 | 2/2007 | Beyar et al. | |
| 2007/0055266 A1 | 3/2007 | Osorio et al. | |
| 2007/0055267 A1 | 3/2007 | Osorio et al. | |
| 2007/0055278 A1 | 3/2007 | Osorio et al. | |
| 2007/0055280 A1 | 3/2007 | Osorio et al. | |
| 2007/0055284 A1 | 3/2007 | Osorio et al. | |
| 2007/0055285 A1 | 3/2007 | Osorio | |
| 2007/0055300 A1 | 3/2007 | Osorio et al. | |
| 2007/0060941 A1 | 3/2007 | Reiley et al. | |
| 2007/0118142 A1 | 5/2007 | Krueger | |
| 2007/0142842 A1 | 6/2007 | Krueger | |
| 2007/0197935 A1 | 8/2007 | Reiley et al. | |
| 2007/0198013 A1 | 8/2007 | Foley et al. | |
| 2007/0198023 A1 | 8/2007 | Sand et al. | |
| 2007/0198024 A1 | 8/2007 | Plishka et al. | |
| 2007/0255282 A1 | 11/2007 | Simonton et al. | |
| 2007/0282443 A1 | 12/2007 | Globerman et al. | |
| 2008/0039856 A1 | 2/2008 | DiMauro | |
| 2008/0044374 A1 | 2/2008 | Lavergne et al. | |
| 2008/0058827 A1 | 3/2008 | Osorio et al. | |
| 2008/0065087 A1 | 3/2008 | Osorio et al. | |
| 2008/0065089 A1 | 3/2008 | Osorio et al. | |
| 2008/0065137 A1 | 3/2008 | Boucher et al. | |

(56) References Cited

U.S. PATENT DOCUMENTS

| | | |
|---|---|---|
| 2008/0065142 A1 | 3/2008 | Reiley et al. |
| 2008/0065190 A1 | 3/2008 | Osorio et al. |
| 2008/0071283 A1 | 3/2008 | Osorio et al. |
| 2008/0086133 A1 | 4/2008 | Kuslich et al. |
| 2008/0132935 A1 | 6/2008 | Osorio et al. |
| 2008/0140079 A1 | 6/2008 | Osorio et al. |
| 2008/0140084 A1 | 6/2008 | Osorio et al. |
| 2008/0200915 A1 | 8/2008 | Globerman et al. |
| 2008/0212405 A1 | 9/2008 | Globerman et al. |
| 2008/0228192 A1 | 9/2008 | Beyar et al. |
| 2009/0264892 A1 | 10/2009 | Beyar et al. |
| 2009/0264942 A1 | 10/2009 | Beyar et al. |
| 2009/0270872 A1 | 10/2009 | DiMauro |
| 2010/0065154 A1 | 3/2010 | Globerman |
| 2010/0069786 A1 | 3/2010 | Globerman |
| 2010/0152855 A1 | 6/2010 | Kuslich et al. |
| 2010/0168271 A1 | 7/2010 | Beyar |
| 2010/0268231 A1 | 10/2010 | Kuslich et al. |
| 2012/0307586 A1 | 12/2012 | Globerman et al. |
| 2013/0123791 A1 | 5/2013 | Beyar et al. |
| 2013/0261217 A1 | 10/2013 | Beyar et al. |
| 2013/0345708 A1 | 12/2013 | Beyar et al. |
| 2014/0088605 A1 | 3/2014 | Ferreyro et al. |
| 2015/0122691 A1 | 5/2015 | Globerman et al. |
| 2015/0127058 A1 | 5/2015 | Beyar et al. |
| 2015/0148777 A1 | 5/2015 | Ferreyro et al. |
| 2016/0051302 A1 | 2/2016 | Ferreyro et al. |
| 2016/0235459 A1 | 8/2016 | Globerman et al. |
| 2017/0216483 A1 | 8/2017 | Beyar et al. |

FOREIGN PATENT DOCUMENTS

| | | |
|---|---|---|
| CN | 1138001 A | 12/1996 |
| CN | 1310026 A | 8/2001 |
| DE | 136018 C | 11/1902 |
| DE | 226956 | 3/1909 |
| DE | 868497 C | 2/1953 |
| DE | 1283448 | 11/1968 |
| DE | 1810799 | 6/1970 |
| DE | 2821785 | 11/1979 |
| DE | 3003947 | 8/1980 |
| DE | 2947875 | 4/1981 |
| DE | 3443167 | 6/1986 |
| DE | 8716073 | 3/1988 |
| DE | 3817101 | 11/1989 |
| DE | 3730298 | 2/1990 |
| DE | 4104092 | 8/1991 |
| DE | 293485 | 9/1991 |
| DE | 4016135 | 3/1992 |
| DE | 4315757 | 11/1994 |
| DE | 19612276 | 10/1997 |
| DE | 10258140 | 7/2004 |
| EP | 20207 | 6/1908 |
| EP | 486638 | 6/1938 |
| EP | 0044877 | 2/1982 |
| EP | 0190504 | 3/1986 |
| EP | 0177781 | 4/1986 |
| EP | 0 235 905 A1 | 9/1987 |
| EP | 0235905 | 9/1987 |
| EP | 0301759 | 7/1988 |
| EP | 0242672 | 9/1989 |
| EP | 0493789 | 6/1990 |
| EP | 0425200 | 10/1990 |
| EP | 0423916 | 4/1991 |
| EP | 0475077 | 3/1992 |
| EP | 0511868 | 4/1992 |
| EP | 0581387 | 2/1994 |
| EP | 0614653 | 9/1994 |
| EP | 0669100 | 8/1995 |
| EP | 0748615 | 12/1996 |
| EP | 0763348 | 3/1997 |
| EP | 1 074 231 A1 | 2/2001 |
| EP | 1074231 | 2/2001 |
| EP | 1095667 | 5/2001 |
| EP | 1103237 | 5/2001 |
| EP | 1104260 | 6/2001 |
| EP | 1 247 454 A1 | 10/2002 |
| EP | 1464292 | 10/2004 |
| EP | 1 517 655 A1 | 3/2005 |
| EP | 1148850 | 4/2005 |
| EP | 1552797 | 7/2005 |
| EP | 1570873 | 9/2005 |
| EP | 1 596 896 A2 | 11/2005 |
| EP | 1598 015 | 11/2005 |
| EP | 1148851 | 5/2006 |
| EP | 1829518 | 9/2007 |
| EP | 1 886 648 A1 | 2/2008 |
| EP | 1886647 | 2/2008 |
| FR | 1548575 | 10/1968 |
| FR | 2606282 | 5/1988 |
| FR | 2629337 | 10/1989 |
| FR | 2638972 | 5/1990 |
| FR | 2674119 | 9/1992 |
| FR | 2690332 | 10/1993 |
| FR | 2712486 | 5/1995 |
| FR | 2722679 | 1/1996 |
| GB | 8331 | 0/1904 |
| GB | 179502045 | 4/1795 |
| GB | 190720207 A | 6/1908 |
| GB | 408668 | 4/1934 |
| GB | 486638 A | 6/1938 |
| GB | 2114005 | 8/1983 |
| GB | 2156824 | 10/1985 |
| GB | 2197691 | 5/1988 |
| GB | 2268068 | 1/1994 |
| GB | 2276560 | 10/1994 |
| GB | 2411849 | 9/2005 |
| GB | 2413280 | 10/2005 |
| GB | 2469749 | 10/2010 |
| JP | S51-134465 A | 11/1976 |
| JP | 54-009110 | 1/1979 |
| JP | 55-009242 U | 1/1980 |
| JP | 55-109440 | 8/1980 |
| JP | 62-068893 | 3/1987 |
| JP | 63-194722 A | 8/1988 |
| JP | 02-122017 | 5/1990 |
| JP | 02-166235 | 6/1990 |
| JP | 02-125730 U | 10/1990 |
| JP | 4 329956 | 11/1992 |
| JP | 07-000410 | 1/1995 |
| JP | 8322848 | 12/1996 |
| JP | 10146559 | 6/1998 |
| JP | 10-511569 | 10/1998 |
| JP | 2001-514922 A | 9/2001 |
| JP | 2004-16707 | 1/2004 |
| JP | 2005-500103 A | 1/2005 |
| JP | 2008-55367 | 3/2008 |
| RO | 116784 | 6/2001 |
| RU | 662082 | 5/1979 |
| RU | 1011119 | 4/1983 |
| RU | 1049050 | 10/1983 |
| WO | 88/10129 A1 | 12/1988 |
| WO | WO 90/00037 | 1/1990 |
| WO | WO 92/14423 | 9/1992 |
| WO | WO 94/12112 | 6/1994 |
| WO | WO 95/13862 | 5/1995 |
| WO | WO 96/11643 | 4/1996 |
| WO | WO 96/19940 | 7/1996 |
| WO | WO 96/32899 | 10/1996 |
| WO | WO 96/37170 | 11/1996 |
| WO | WO 97/18769 | 5/1997 |
| WO | WO 97/28835 | 8/1997 |
| WO | WO 98/28035 | 7/1998 |
| WO | WO 98/38918 | 9/1998 |
| WO | WO 99/18866 | 4/1999 |
| WO | WO 99/18894 | 4/1999 |
| WO | WO 99/29253 | 6/1999 |
| WO | WO 99/37212 | 7/1999 |
| WO | WO 99/39661 | 8/1999 |
| WO | WO 99/49819 | 10/1999 |
| WO | WO 99/52446 | 10/1999 |
| WO | WO 00/06216 | 2/2000 |
| WO | WO 00/44319 | 8/2000 |
| WO | WO 00/44321 | 8/2000 |

(56) References Cited

FOREIGN PATENT DOCUMENTS

| | | |
|---|---|---|
| WO | WO 00/44946 | 8/2000 |
| WO | WO 00/54705 | 9/2000 |
| WO | WO 00/56254 | 9/2000 |
| WO | WO 2001/008571 | 2/2001 |
| WO | WO 01/013822 | 3/2001 |
| WO | WO 01/54598 | 8/2001 |
| WO | WO 01/060270 | 8/2001 |
| WO | WO 01/76514 | 10/2001 |
| WO | WO 02/00143 | 1/2002 |
| WO | WO 02/02033 | 1/2002 |
| WO | WO 02/19933 | 3/2002 |
| WO | 02/064195 A2 | 8/2002 |
| WO | WO 02/064062 | 8/2002 |
| WO | WO 02/064194 | 8/2002 |
| WO | WO 02/072156 | 9/2002 |
| WO | WO 02/096474 | 12/2002 |
| WO | WO 03/007854 | 1/2003 |
| WO | WO 03/015845 | 2/2003 |
| WO | WO 03/022165 | 3/2003 |
| WO | WO 2003/061495 | 7/2003 |
| WO | WO 03/078041 | 9/2003 |
| WO | WO 03/101596 | 12/2003 |
| WO | WO 04/002375 | 1/2004 |
| WO | WO 2004/019810 | 3/2004 |
| WO | WO 2004/071543 | 8/2004 |
| WO | WO 2004/075965 | 9/2004 |
| WO | WO 2004/080357 | 9/2004 |
| WO | WO 2004/110292 | 12/2004 |
| WO | WO 2004/110300 | 12/2004 |
| WO | WO 05/000138 | 1/2005 |
| WO | 2005/017000 A1 | 2/2005 |
| WO | WO 2005/032326 | 4/2005 |
| WO | WO 2005/048867 | 6/2005 |
| WO | WO 2005/051212 | 6/2005 |
| WO | WO 2005/110259 | 11/2005 |
| WO | WO 2006/011152 | 2/2006 |
| WO | WO 2006/039159 | 4/2006 |
| WO | 2006/062939 A2 | 6/2006 |
| WO | WO 2006/090379 | 8/2006 |
| WO | WO 07/015202 | 2/2007 |
| WO | WO 07/036815 | 4/2007 |
| WO | WO 2007/148336 | 12/2007 |
| WO | WO 2008/004229 | 1/2008 |
| WO | WO 08/032322 | 3/2008 |
| WO | WO 08/047371 | 4/2008 |

OTHER PUBLICATIONS

Lu Orthopedic Bone Cement. Biomechanics and Biomaterials in Orthopedics. Ed. Poitout London: Springer-Verlag London Limited 2004 86-88.
Japanese Office Action dated Dec. 6, 2011 for Application No. 2008-524651 (9 Pages).
Mendizabal et al., Modeling of the curing kinetics of an acrylic bone cement modified with hydroxyapatite. International Journal of Polymeric Materials. 2003;52:927-938.
Morejon et al., Kinetic effect of hydroxyapatite types on the polymerization of acrylic bone cements. International Journal of Polymeric Materials. 2003;52(7):637-654.
Sreeja et al., Studies on poly(methyl methacrylate)/polystyrene copolymers for potential bone cement applications. Metals Materials and Processes. 1996;8(4):315-322.
Yang et al., Polymerization of acrylic bone cement investigated by differential scanning calorimetry: Effects of heating rate and TCP content. Polymer Engineering and Science. Jul. 1997;1182-1187.
Al-Assir, et al., "Percutaneous Vertebroplasty: A Special Syringe for Cement Injection," AJNR Am. J. Neuroradiol. 21:159-61 (Jan. 2000).
Amar, Arun P. et al., "Percutaneous Transpedicular Polymethylmethacrylate Vertebroplasty for the Treatment of Spinal Compression Fractures," Neurosurgery 49(5):1105-15 (2001).

Andersen, M. et al., "Vertebroplastik, ny behandling af osteoporotiske columnafrakturer?", Ugeskr Laefer 166/6:463-66 (Feb. 2, 2004).
Avalione & Baumeister III, Marks' Standard Handbook for Mechanical Engineers, 10 ed, pp. 5-6 (1996).
Barr, J.D., "Percutaneous Vertebroplasty for pain Relief and Spinal Stabilization," Spine 25(8):923-28 (2000).
Belkoff, S. et al., The Biomechanics of Vertebroplasty, the Effect of Cement Volume on Mechanical Behavior, SPINE 26(14):1537-41 (2001).
Belkoff, S.M. et al., "An Ex Vivo Biomechanical Evaluation of a Hydroxyapatite Cement for Use with Kyphoplasty," Am. J. Neurorad. 22:1212-16 (2001).
Belkoff, S.M. et al., "An Ex Vivo Biomechanical Evaluation of a Inflatable Bone Tamp Used in the Treatment of Compression Fracture," SPINE 26(2):151-56 (2001).
Belkoff, S.M. et al., "An in Vitro Biomechanical Evaluation of Bone Cements Used in Percutaneous Vertebroplasty, " Bone 25(2):23S-26S (1999).
Blinc, A et al., "Methyl-methacrylate bone cement surface does not promote platelet aggregation or plasma coagulation in vitro," Thrombosis Research 114:179-84 (2004).
Bohner, M. et al., "Theoretical and Experimental Model to Describe the Injection of a Polymethacrylate Cement into a Porous Structure," Biomaterials 24(16):2721-30 (2003).
Breusch, S. et al., "Knochenzemente auf Basis von Polymethylmethacrylat," Orthopade 32:41-50 (2003) w/ abs.
Carrodegus et al., "Injectable Acrylic Bone Cements for Vertebroplasty with Improved Properties," J. Biomed. Materials Res. 68(1):94-104 (Jan. 2004).
Codman & Shurtleff, "V-MAX™ Mixing and Delivery Device," Catalog No. 43-1056.
Combs, S. et al., "The Effects of Barium Sulfate on the Polymerization Temperature and Shear Strength of Surgical Simplex P," Clin. Ortho. and Related Res. pp. 287-291 (Jun. 4, 1979).
Cotton, A. et al., "Percutaneous Vertebroplasty: State of the Art," Scientific Exhibit, Radiographics 18:311-20 (1998).
Dean, J.R. et al., "The Strengthening Effect of Percutaneous Vertebroplasty," Clin Radiol. 55:471-76 (2000).
Deramond, H. et al, "Percutaneous Vertebroplasty with Polymethylmethacrylate, Technique Indications and Results," Radiologic Clinics of North America 36(3) (May 1988).
Deramond, H. et al., "Temperature Elevation Caused by Bone cement Polymerization During Vertbroplasty," Bone 25(2):17S-21S (1999).
DeWijn, J.R., Characterization of Bone Cements, The Institute of Dental Materials Science and Technology and the Dept of Ortho., Catholic University, Netherlands 46:38-51 (1975).
European Search Report, from EP05763930.4; dated Sep. 11, 2008.
European Search Report, from EP09151379.6, dated Oct. 20, 2009.
European Search Report, from EP06780252.0, dated Oct. 29, 2009.
Farrar, D.F. et al., "Rheological Properties of PMMA Bone Cements During Curing," Biomaterials 22:3005-13 (2001).
Fessler, Richard D. et al., "Vertebroplasty," Neurosurgical Operative Atlas 9:233-240 (2000).
Gangi, A., "CT-Guided Interventional Procedures for Pain Management in the Lumbosacral Spine," Radiographics 18:621-33 (1998).
Gangi, A., "Computed Tomography CT and Fluoroscopy-Guided Vertebroplasty: Results and Complications in 187 Patients," Seminars in Interventional Radiology 16(2):137-42 (1999).
Gangi, A., "Percutaneous Vertebroplasty Guided by a Combination of CT and Fluoroscopy," AJNR 15:83-86 (1994).
Garfin, S. R. et al., "New Technologies in Spine, Kyphoplasty and Vertebroplasty for the Treatment of Painful Osteoporotic Compression Fractures," Spine 26(14:1511-15 (2001).
Gheduzzi, S. et al., "Mechanical Characterisation of Three Percutaneous Vertebroplasty Biomaterials," J. Mater Sci Mater Med 17(5):421-26 (2006).
Giannitsios, D. et al., "High Cement Viscosity Reduces Leakage Risk in Vertebroplasty," European Cells & Mat. 10 supp. 3:54 (2005).

(56) References Cited

OTHER PUBLICATIONS

Grados F. et al.,"Long-Term Observations of Vertebral Osteoporotic Fractures Treated by Percutaneous Vertebroplasty," Rheumatology 39:1410-14 (2000).
Hasenwinkel, J. et al., "A Novel High-Viscosity, Two-Solution Acrylic Bone Cement: Effect of Chemical Composition on Properties," J. Biomed. Materials Research 47(1):36-45 (1999).
Hasenwinkel, J. et al., "Effect of Initiation Chemistry on the Fracture Toughness, Fatigue Strength, and Residual Monomer Content of a Novel High-Viscosity, Two-Solution Acrylic Bone Cement," J. Biomed. Materials Res. 59(3):411-21 (2001).
Heini, P. et al., "Augmentation of Mechanical Properties in Osteoporatic Vertebral Bones—a Biomechanical Investigation of Vertebroplasty Efficacy With Different Bone Cements," EUR Spine J. v. 10, pp. 164-171, Springer-Verlag (2001).
Heini, P., "Percutaneous Transpedicular Vertebroplasty with PMMA: Operative Technique and Early Results," EUR Spine J. v. 9, pp. 445-450, Springer-Verlag (2000).
Heraeus Palacos R, 2008, Palacos R, high Viscosity Bone Cement.
International Preliminary Report on Patentability, from PCT/IB06/053014, dated Apr. 10, 2008.
International Search Report, from PCT/IL06/00239, dated Jan. 26, 2007.
International Search Report, from PCT/IL05/00812, dated Feb. 28, 2007.
International Search Report, from PCT/IB06/052612, dated Oct. 2, 2007.
International Search Report, from PCT/IL07,00833, dated Apr. 4, 2008.
International Search Report, from PCT/IL07/00484, dated Apr. 17, 2008.
International Search Report, for PCT/MX03/000027, filed Mar. 14, 2003.
Jasper, L.E. et al., "The Effect of Monomer-to-Powder Ratio on the Material Properties of Cranioplastic," Bone 25(2):27S-29S (1999).
Jensen, Mary E. et al., "Percutaneous Polymethylmethacrylate Vertebroplasty in the Treatment of Osteoporotic Vertebral Body Compression Fractures: Technical Aspects," AJNR 18:1897-1904 (1997).
Jensen, Mary E. et al., "Percutaneous Vertebroplasty in the Treatment of Osteoporotic Compression Fractures," Spine Interventions 10(3):547-568 (2000).
Johnson & Johnson Orthopaedics, The CEMVAC Method, Raynham, MA.
Kallmes, D. et al., "Radiation Dose to the Operator During Vertebroplasty: Prospective Comparison of the Use of 1-cc Syringes Versus an Injection Device," AJNR Am. J. Neuroradiol. 24:1257-60 (2003).
Kaufmann et al, "Age of Fracture and Clinical Outcomes of Percutaneous Vertebroplasty," Am. J. Neuroradiology 22:1860-63 (2001).
Kuhn, Klaus-Dieter, Bone Cements—Uptodate Comparison of Physical and Chemical Properties of Commercial Materials, Springer-Verlag Heidelberg Germany p. 7-8, 17, 38 (2000).
Kyphom Medical Professionals, KyphXProducts (Nov. 8, 2001).
Lewis, G. et al., "Rheological Properties of Acrylic Bone Cement During Curing and the Role of the Size of the Powder Particles," J. Biomed. Mat. Res. Appl. Biomat. 63(2):191-99 (2002).
Li, C. et al., "Thermal Characterization of PMMA-Based Bone Cement Curing," J. Materials Sci.: Materials in Medicine 15:84-89 (2004).
Lieberman, I.H. et al., "Initial Outcome and Efficacy of Kyphoplasty in the Treatment of Painful Osteoporatic Vertebral Compression Fractures," Spine 26(14:1631-38 (2001).
Mathis, John et al., "Percutaneous Vertebroplasty: A Developing Standard of Care for Vertebral Compression Fractures," AJNR Am. J. Neurorad. 22:373-81 (2001).
Medsafe Palacos R 2007, Data Sheet: Palacos R Bone cemember with Garamycin pp. 1-7; http://www.medsafe.govt.nz/profs/datasheet/p/palacosbonecements.htm.
Mousa, W.F. et al., "Biological and Mechanical Properties of PMMA-Based Bioactive Bone Cements," Biomaterials 21:2137-46 (2000).
O'Brien, J. et al., "Vertebroplasty in patients with Severe Vertebral Compression Fractures: A Technical Report," AJNR 21:1555-58 (2000).
Odian, G., "Principles of Polymerization," pp. 20-23.
Padovani, B. et al., "Pulmonary Embolism Caused by Acrylic Cement: A Rare Complication of Percutaneous Vertebroplasty," AJNR 20:375-77 (1999).
Parallax Medical, Inc., Exflow Cement Delivery System (May 16, 2000).
Pascual, B. et al., "New Aspects of the Effect of Size and Size Distribution on the Setting Parameters and Mechanical Properties of Acrylic Bone Cememnts," Biomaterials 17(5)509-16 (1996).
Rimnac, CM, et al., "The effect of centrifugation on the fracture properties of acrylic bone cements," JB&JS 68A(2):281-87 (1986).
Robinson, R. et al., "Mechanical Properties of Poly(methyl methacrylate) Bone Cement," J. Biomed. Materials Res. 15(2):203-08 (2004).
Ryu, K. S. et al., "Dose-Dependent Epidural Leakage of Polymethylmethacrylate after Percutaneous Vertebroplasty in Patients with Osteoporotic Vertebral Compression Fractures," J. Neuro: Spine 96:56-61 (2002).
Saha, S. et a., "Mechanical Properties of Bone Cement: A Review," J. Biomed. Materials Res. 18(4):435-62 (1984).
Serbetci, K. et al., "Thermal and Mechanical Properties of Hydroxyapatite Impregnated Acrylic Bone Cements," Polymer Testing 23:145-55 (2004).
Shah, T., Radiopaque Polymer Formulations for Medical Devices; Medical Plastics and Biomaterials Special Section; Medical device & Diagnostic Industry pp. 102-111 (2000).
Supp. EP Search Report, from EP Appl. No. 05763930.4, dated Sep. 11, 2008.
Supp. EP Search Report, from EP Appl. No. 06711221.9, dated Sep. 15, 2008.
Vasconcelos, C., "Transient Arterial Hypotension Induced by Polymethyacrylated Injection During Percutaneous Vertebroplasty," Letter to the Editor, JVIR (Aug. 2001).
Wimhurst, J.A., et al., "The Effects of Particulate Bone Cements at the Bone-Implant Interface," J. Bone & Joint Surgery pp. 588-592 (2001).
Wimhurst, J.A. et al., "Inflammatory Responses of Human Primary Macrophages to Particulate Bone Cements in Vitro," J. Bone & Joint Surgery 83B:278-82 (2001).
Zapalowicz, K. et al., "Percutaneous Vertebroplasty with Bone Cement in the Treatment of Osteoporotic Vertebral Compression Fractures," Ortopedia Traumatologia Rehabilitacja NR Jan. 2003.
Japanese Office Action dated Feb. 21, 2012 for Application No. 2009-516062 (6 Pages).
Baroud, G., "Influence of Mixing Method on the Cement Temperature-Mixing Time History and Doughing Time of Three Acrylic Cements for Vertebroplasty," Wiley Periodicals Inc. 112-116 (2003).
European Search Report, from EP 10182769.9, dated Mar. 2, 2011.
European Search Report, from EP 10182693.1, dated Mar. 2, 2011.
European Search Report, from EP 10192302.7, dated Mar. 24, 2011.
European Search Report, from EP 10192301.9, dated Mar. 24, 2011.
European Search Report, from EP 10192300.1, dated Mar. 24, 2011.
Hide, I. et al., "Percutaneous Vertebroplasty: History, Technique and current Perspectives," Clin. Radiology 59:461-67 (2004).
Hu, M. et al., "Kyphoplasty for Vertebral Compression Fracture Via a Uni-Pedicular Approach,"Pain Phys. 8:363-67 (2005).
Liang, B. et al., "Preliminary Clinical Application of Percutaneous Vertebroplasty," Zhong Nan Da Xue Bao Yi Xue Ban 31(1):114-9 (2006)(abs. only).
Noetzel, J. et al., Calcium Phosphate Cements in Medicine and Denistry—A Review of Literature, Schweiz Monatsschr Zehmed 115(12):1148-56 (2005)(abs. only).
Supp. EP Search Report, from EP Appl. No. 07766863.0, dated Apr. 12, 2011.
Australian Office Action dated Mar. 7, 2013 for Application No. 2012203300 (6 pages).

(56) References Cited

OTHER PUBLICATIONS

Japanese Office Action dated Apr. 9, 2013 for Application No. 2007-556708.
Kuehn et al., Acrylic bone cements: composition and properties. Orthop Clin North Am. Jan. 2005;36(1):17-28, v.
U.S. Appl. No. 13/722,081, filed Dec. 20, 2012, Methods, Materials and Apparatus for Treating Bone and Other Tissue.
U.S. Appl. No. 13/793,385, filed Mar. 11, 2013, Methods, Materials and Apparatus for Treating Bone and Other Tissue.
International Search Report, for PCT/IL07/00808, dated Aug. 22, 2008.
Marks, Standard handbook for mechanical engineers, section 5 (Tenth ed. 1996).
Supp. EP Search Report, from EP 07766838.2, dated May 18, 2011.
Canale et al. "Campbell's Operative Orthopaedics—vol. three—Ninth edition", Mosby: P. 2097,2121, 2184-2185, 2890-2896, 1998. Abstract.
Cole et al. "AIM Titanium Humeral Nail System", Sugical Technique, DePuy Orthopedics, 17 P., 2000.
Edeland "Some Additional Suggestions for an Intervertebral Disc Prothesis", Journal of Biomedical Engineering, XP008072822, 7(1): 57-62, Jan. 1985. Figs.3a-3d.
Lewis "Properties of Acrylic Bone Cement: State of the Art Review, Journal of Biomedical Materials Research" Applied Biomaterials, 38(2): 155-182, 1997. p. 158, § Viscosity, Table II.
Lewis "Toward Standardization of Methods of Determination of Fracture Properties of Acrylic Bone Cement and Statistical Analysis of Test Results", Journal of Biomedical Research: Applied Biomaterials, 53(6): 748-768, 2000.
Steen "Laser Surface Treatment", Laser Material Processing, Springer, 2nd Ed., Chap.6: 218-271, 2003.
Varela et al. "Closed Intramedullary Pinning of Metacarpal and Phalanx Fractures", Orthopedics, 13(2): 213-215, 1990. Abstract.
Baroud et al. "Injection Biomechanics of Bone Cements Used in Vertebroplasty", Biomedical Maerials and Engineering, 00: 1-18, 2004.
Heini et al. "The Use of a Side-Opening Injection Cannula in Vertebroplasty", Spine, 27(1): 105-109, 2002.
Hernandez et al. "Influence of Powder Particle Size Distribution on Complex Viscosity and Other Properties of Acrylic Bone Cement for Vetebroplasty and Kyphoplasty", Journal of Biomedical Materials Research, Part. B: Applied Biomaterials, 77B: 98-103, 2006.
Ishikawa et al. "Effects of Neutral Sodium Hydrogen Phosphate on Setting Reaction and Mechanical Strength of Hydroxyapatite Putty", Journal of Biomedical Materials Research, 44: 322-329, 199.
Ishikawa et al. "Non-Decay Type Fast-Setting Calcium Phosphate Cement: Hydroxyapatite Putty Containing an Increased Amount of Sodium Alginate", Journal of Biomedical Materials Research, 36: 393-399, 1997.
Krause et al. "The Viscosity of Acrylic Bone Cements", Jouirnal of Biomedical Materials Research, 16: 219-243, 1982.
Nussbaum et al. "The Chemistry of Acrylic Bone Cements and Implications for Clinical Use in Image-Guided Therapy", Journal of Vascular and Interventional Radiology, 15: 121-126, 2004.
Weissman et al. "Trochanteric Fractures of the Femur. Treatment With a Strong Nail and Early Weight-Bearing", Clinical Orthopedics and Related Research, 67: 143-150, 1969. Fig.
Cromer, A., "Fluids," Physics for the Life Sciences, 2:136-37 (1977).
JP Office Action, from JP Appl No. 2008-532910, dated Jul. 19, 2011.
Lindeburg, M., "External Pressurized Liquids," Mechanical Eng. Ref. Manual for the PE Exam, 10:15-14(May 1997).
JP Office Action, from JP Appl No. 2009-517607, dated Aug. 9, 2011.
European Search Report, from EP07827231.7, dated Sep. 12, 2011.
[No Author Listed] Plastic Deformation of Metals and Related Properties. New Age Publishers. p. 1-29.
European Search Report for Application No. 12181745.6, dated Sep. 25, 2012. (9 pages).
Japanese Office Action for Application No. 2009-517607, dated Aug. 28, 2012. (4 pages).
Japanese Office Action for Application No. 2009-516062, dated Oct. 16, 2012 (6 pages).
Feldman, H., "Die Geschichte der Injektionen," Laryngo-Rhino-Othol 79:239-46 (2000).
Glasgow Medico-Chirurgical Society, The lancet 1364 (May 18, 1907).
Greenberg, "Filling Root Canals by an Injection Technique," Dental Digest 61-63 (Feb. 1963).
Greenberg, "Filling Root Canals in Deciduous Teeth by an Injection Technique," Dental Digest 574-575 (Dec. 1961).
Greig, D., "A New Syringe for Injecting Paraffin," The Lancet 611-12 (Aug. 29, 1903).
Lake, R., "The Restoration of the Inferior Turbinate Body by Paraffin Injections in the Treatment of Atrophic Rhinitis," The Lancet 168-69 (Jan. 17, 1903).
Paget, S., "The Uses of Paraffin in Plastic Surgery," The Lancet 1354 (May 16, 1903).
Walton, A, "Some Cases of Bone Cavities Treated by Stopping With Paraffin," The Lancet 155 (Jan. 18, 1908).
U.S. Appl. No. 11/468,421, filed Aug. 30, 2006, Cannula.
U.S. Appl. No. 14/010,933, filed Aug. 27, 2013, Methods, Materials and Apparatus for Treating Bone and Other Tissue.
U.S. Appl. No. 14/091,638, filed Nov. 27, 2013, Hydraulic Device for the Injection of Bone Cement in Percutaneous Vertebroplasty.
Japanese Office Action for Application No. 2009-517607, dated Feb. 4, 2014. (8 pages).
Japanese Office Action for Application No. 2009-517607, dated Aug. 27, 2013. (6 pages).
European Search Report for Application No. 13174874.1, dated Nov. 13, 2013 (6 pages).
Japanese Interrogation for Application No. 2009-516062 (Appeal No. 2013-002371) dated Jul. 9, 2013 (9 Pages).
U.S. Appl. No. 14/057,355, filed Oct. 18, 2013, Device for Delivering Viscous Material.
U.S. Appl. No. 14/591,295, filed Jan. 7, 2015, Fluid Delivery System.
U.S. Appl. No. 14/596,575, filed Jan. 14, 2015, Methods, Materials, and Apparatus for Treating Bone and Other Tissue.
U.S. Appl. No. 14/614,818, filed Feb. 2, 2015, Hydraulic Device for the Injection of Bone Cement in Percutaneous Vertebroplasty.
U.S. Appl. No. 14/929,628, filed Nov. 2, 2015, Hydraulic Device for the Injection of Bone Cement in Percutaneous Vertebroplasty.
U.S. Appl. No. 15/041,572, filed Feb. 11, 2016, Mixing Apparatus.
U.S. Appl. No. 15/491,214, filed Apr. 19, 2017, Bone Cement and Methods of Use Thereof.
[No Author Listed] Simplex P Bone Cement. Stryker Corporation, 2 pages, publication date unknown. Retrieved from <http://www.stryker.com/en-us/products/Orthopaedics/BoneCementSubstitutes/index.htm>.
[No Author Listed] Standard Specification for Acrylic Bone Cement. Designation F 451-08, ASTM International (2008), 11 pages.
Chinese Office Action for Application No. 201310064546.9, dated Jul. 31, 2014 (24 pages).
Chinese Office Action for Application No. 201510099411.5, dated Aug. 16, 2017 (10 pages).
European Communication dated Jul. 1, 2015 for Application No. 10182769.9, enclosing third party observations concerning patentability (Submission dated Jun. 25, 2015) (6 pages).
Notice of Opposition to a European Patent for Patent No. 2314259, from KIPA AB (EP Application No. 10182769.9), dated Apr. 28, 2016 (72 pages).
Notice of Opposition to a European Patent for Patent No. 2314259, from Loyer & Abello (EP Application No. 10182769.9), dated Apr. 28, 2016 (40 pages).
European Communication for Application No. 10192301.9, dated Sep. 17, 2015, enclosing third party observations concerning patentability (Submission dated Sep. 11, 2015 (22 pages).

(56) References Cited

OTHER PUBLICATIONS

Extended European Search Report for Application No. 14166420.1, dated Jul. 14, 2014 (9 pages).
Extended European Search Report for Application No. 16173186.4, dated Oct. 6, 2016 (11 pages).
Su, W.-F, Polymer Size and Polymer Solutions. Principles of Polymer Design and Synthesis. Chapter 2, pp. 9-26, Springer-Verlag Berlin Heidelberg, 2013.
U.S. Appl. No. 13/571,802, filed Aug. 10, 2012, Mixing Apparatus.
[No Author Listed] ASTM Designation F 451-99a ϵ1, Standard Specification for Acrylic Bone Cement, editorially corrected Jun. 2003.
[No Author Listed] "Bone Cement—History, Performance, and Choice," Technical Monograph, DePuy Synthes Joint Reconstruction, 2014.
[NoAuthorListed] Definition of "facilitate," extracted from LONGMAN, Dictionary of Contemporary English, 2009.
[No Author Listed] DePuy CMW Heritage Bone Cements, Product Information, © 2016, DePuy Synthes, Johnson & Johnson Medical Limited; brochure issued Oct. 2016.
[No Author Listed] ISO 5883:2002(e), © ISO 2002, downloaded Sep. 2, 2005.
Argenson, J-N et al., "The Effect of Vancomycin and Tobramycin on the Tensile Properties of Cured Low Viscosity Bone Cements," Eur J Exp Musculoskel Res, 1994, v. 3, pp. 43-47.
Submission in Opposition Proceedings in European Patent No. 2314259, by Loyer & Abello, dated Sep. 20, 2017 (10 pages).
Submission in Opposition Proceedings in European Patent No. 2314259, by KIPA AB, dated Sep. 21, 2017 (16 pages).
Noble, P. C. et al., "Penetration of Acrylic Bone Cements into Cancellous Bone," Acta Orthop Scand, 1983, v. 54, pp. 566-573.
Spierings, Pieter T. J., "Properties of Bone Cement Testing and Performance of Bone Cements," 2005, Springer Link, chapter 3.3.

\* cited by examiner

TEMPERATURE CONTROL SYSTEM

RELATED APPLICATIONS

The present application claims the benefit under 35 USC 119(e) of U.S. provisional applications No. 60/814,559, filed on Jun. 19, 2006 and entitled "Method and Apparatus for Extending the Working Time of Bone Filler Materials", No. 60/765,484, filed on Feb. 2, 2006 and entitled "Methods, Materials and Apparatus for Treating Bone and Other Tissue", No. 60/762,789, filed on Jan. 26, 2006 and entitled "Methods, Materials and Apparatus for Treating Bone and Other Tissue", No. 60/738,556, filed on Nov. 22, 2005 and entitled "Methods, Materials and Apparatus for Treating Bone and Other Tissue", the disclosures of all of which are fully incorporated herein by reference.

The present application is a Continuation in Part of U.S. application Ser. No. 11/461,072, filed on Jul. 31, 2006 and entitled "Bone Cement and Methods of Use Thereof", which is a Continuation in Part of U.S. application Ser. No. 11/360,251 filed on Feb. 22, 2006 and entitled "Methods, Materials and Apparatus for Treating Bone and Other Tissue". The present application is also a Continuation in Part of PCT/IL2006/000239, filed on Feb. 22, 2006 and entitled "Methods, Materials and Apparatus for Treating Bone and Other Tissue" and published as WO 2006/090379, which is currently pending and is a Continuation in Part of U.S. application Ser. No. 11/194,411, filed on Aug. 1, 2005 and entitled "Methods, Materials and Apparatus for Treating Bone and Other Tissue", the disclosures of all of which are fully incorporated herein by reference.

The present application claims priority from IL174347, filed on Mar. 16, 2006 and entitled "Bone Cement and Methods of Use Thereof" which is currently pending, the disclosure of which is fully incorporated herein by reference.

FIELD OF THE INVENTION

The present invention relates to controlling a temperature of a reaction mixture to assure that the reaction will not reach a desired degree of completion before a specified time.

BACKGROUND OF THE INVENTION

Orthopedic procedures such as, for example, Vertebroplasty or Kyphoplasty include injection of setting material while they are still in an un-set condition. Setting of the material prior to completion of the procedure can delay completion of the procedure and/or cause medical complications.

Typically, bone cement employed in Vertebroplasty and/or Kyphoplasty comprises an acrylic mixture including a polymer component and a monomer component (e.g. polymethylmetacrylate [PMMA] and monomethylmethacrylate [MMA]). Acrylic bone cements generally set, or harden, rapidly after mixing of the polymer and monomer components. The short amount of time between mixing and full setting defines a "window" of time during which the material must be prepared, loaded into an appropriate delivery device and delivered into the subject. For standard acrylic bone cements, this window is only a few minutes long.

A window of time which is too small can be inconvenient, for example if a long procedure is planned (e.g. treatment of two or more vertebrae in a single operation) and/or if an unplanned delay occurs.

In some medical procedures, high viscosity cements are employed. High viscosity at the time of injection can contribute to a reduction in the risk of cement leakage, while sustaining an ability to infiltrate into the intravertebral cancellous bone (interdigitaion) [see G Baroud et al, Injection biomechanics of bone cements used in vertebroplasty, Bio-Medical Materials and Engineering 00 (2004) 1-18].

In some cases, cements characterized by a high viscosity at the time of injection will set shortly after reaching the high viscosity.

U.S. application Ser. No. 10/549,409 to Ferreyro-Irigoyen et al. describes maintaining a bone cement loaded syringe in a cold atmosphere to slow time of solidification of the cement. The disclosure of this application is fully incorporated herein by reference.

It is known in the art, that reducing the temperature of a polymerization reaction reduces the polymerization rate. In the context of bone cement, this principle has led to the practice of cooling one or more of the polymer component and the monomer component prior to mixing. Cooling is typically done in a refrigerator. Generally, the refrigerator is located outside the operating theater where the cement components are typically mixed. Cooling of components of the polymerization reaction mixture prior to mixing can delay polymerization to a limited extent, however the delay is uncontrollable once mixing begins and the amount of delay cannot be accurately predicted.

If a refrigerator outside the operating theatre is used, warming of the components can occur while they are being moved from the refrigerator to the operating theatre.

Additionally, since polymerization reactions are typically exothermic, any advantage offered by cooling mixture components prior to mixing is typically lost once the polymerization reaction begins to generate heat.

SUMMARY OF THE INVENTION

A broad aspect of some embodiments of the invention relates to retarding setting kinetics of self-setting bone filler materials after components thereof are mixed. In an exemplary embodiment of the invention, retarding of setting kinetics is carried out in a sterile environment. Optionally, retarding of setting kinetics increases safety by reducing a risk of premature setting. "Setting" as used in this specification and the accompanying claims refers to hardening. A bone filler material is deemed "set" when it has hardened to a point where it cannot be used with an available delivery system.

An aspect of some embodiments of the invention relates to choosing a desired setting time for a bone filler material mixture and implementing the chosen time using temperature control. In an exemplary embodiment of the invention, the mixture includes a polymer such as polymethylmethacrylate (PMMA) and a monomer such as methylmethacrylate (MMA). In an exemplary embodiment of the invention, temperature control includes cooling the mixture. Optionally, the chosen time considers a surgical procedure and/or particulars of the patient. For example the chosen setting time might correspond to an assured minimum working time for a kyphoplasty or vertebroplasty procedure. Optionally, a composition of the mixture can also be varied to influence setting time.

An aspect of some embodiments of the invention relates to controlling the temperature of a bone filler material (e.g. cement) mixture being prepared in an operating theater. In an exemplary embodiment of the invention, the controlling includes cooling. Optionally, controlling is implemented during mixing and/or injection of the filler material. Optionally controlling continues while the filler material is in the sterile field.

In an exemplary embodiment of the invention, an apparatus with an input (e.g. knob or button) calibrated in units of time (e.g. minutes or seconds) provided to cool the mixture and assure the chosen minimum working time. Optionally, the input is connected to a thermostat which regulates a cooling mechanism.

In an exemplary embodiment of the invention, an apparatus is factory calibrated to cool the mixture and assure the chosen minimum working time so that a user operates an "ON" switch (e.g. power switch or gas valve) to activate cooling. Optionally, the input on switch is connected to a thermostat which regulates a cooling mechanism and/or to circuitry which implements a cooling program.

In an exemplary embodiment of the invention, a controller implements the chosen time by receiving input data pertaining at least to the chosen working time, and outputting instructions to a cooling mechanism. Optionally the controller also receives input data pertaining to a reaction mixture.

In an exemplary embodiment of the invention, a user employs a look-up-table of guaranteed setting times by temperature for a bone filler material mixture. Optionally, the table provides setting time/temperature information for several mixtures. Optionally, the several mixtures are based on common components. Optionally, the look-up table is stored in control circuitry.

In an exemplary embodiment of the invention, components of a bone filler material mixture are provided together with a temperature control apparatus in a kit. Optionally, the temperature control apparatus includes an input device calibrated in units of setting time.

In an exemplary embodiment of the invention, there is provided a method of regulating a setting time of a bone filler material, the method comprising:
 (a) combining at least two filler material components to form a biocompatible mixture;
 (b) choosing a setting time for the mixture; and
 (b) regulating a temperature of the mixture to influence reaction kinetics so that the mixture does not set before the chosen setting time.
 Optionally, the regulating a temperature includes cooling.
 Optionally, the cooling is temporally uniform.
 Optionally, the cooling is temporally non-uniform.
 Optionally, the choosing is based upon a predicted time for a medical procedure.
 Optionally, the regulating begins during the combining.
 Optionally, the method is performed under sterile conditions.

In an exemplary embodiment of the invention, there is provided an apparatus for regulating setting time of a bone filler material, the apparatus comprising:
 (a) a cooling mechanism adapted to cool a bone filler material mixture; and
 (b) control circuitry adapted to output a control signal to the cooling mechanism so that the mixture does not set before a minimum setting time.
 Optionally, the control circuitry is adapted to receive a data input pertaining to a minimum setting time.
 Optionally, the apparatus comprises:
 (c) a data input device calibrated in units of minimum setting time.
 Optionally, the data input device is calibrated with a continuous time scale.
 Optionally, the data input device is calibrated in discrete time increments.
 Optionally, the apparatus comprises:
 (c) a data input device adapted for input of data pertaining to the mixture.
 Optionally, the data pertains to a ratio of components of the mixture.
 Optionally, the data pertains to a volume of the mixture.
 Optionally, the data pertains a chemical composition of the mixture.
 Optionally, the data pertains to physical characteristics of at least one component of the mixture.
 Optionally, the apparatus comprises:
 (c) a sensor adapted to detect a temperature of the mixture and transmit data pertaining to the temperature to the controller.
 Optionally, the control circuitry modifies the control signal responsive to the data pertaining to the temperature.
 Optionally, the apparatus comprises:
 (c) a sensor adapted to detect a viscosity of the mixture and transmit data pertaining to the viscosity to the controller.
 Optionally, the control circuitry modifies the control signal responsive to the data pertaining to the viscosity.
 Optionally, the apparatus is provided as a sterile apparatus.

In an exemplary embodiment of the invention, there is provided a method of increasing a setting time of a bone cement, the method comprising:
 (a) mixing components of a bone cement to form a bone cement mixture;
 (b) cooling the mixture in a sterile field of an operating theater.
 Optionally, the cooling is to a constant temperature.
 Optionally, the cooling is with a constant cooling capacity.
 Optionally, the mixing and cooling overlap temporally.

In an exemplary embodiment of the invention, there is provided a kit comprising:
 (a) components of a bone cement mixture; and
 (b) a temperature control apparatus adapted to influence reaction kinetics of the mixture so that the mixture sets at least one minimum setting time.
 Optionally, the components are provided in sufficient quantity to prepare a cement mixture for a single medical procedure.
 Optionally, the components are provided with mixing instructions to produce different mixtures, each mixture characterized by a range of minimum setting times.
 Optionally, the temperature control apparatus is calibrated in relative units applicable to each specific mixture of the different mixtures to achieve a minimum setting time within the range for that specific mixture.
 Optionally, the temperature control apparatus is calibrated in time units indicative of at least one minimum setting time.

In an exemplary embodiment of the invention, there is provided circuitry adapted to:
 (a) receive a data input pertaining to a minimum setting time of a reaction mixture; and
 (b) compute temperature conditions under which the mixture will not set before the minimum setting time.
 Optionally, the circuitry is adapted to:
 (c) receive an additional data input pertaining to the mixture.

BRIEF DESCRIPTION OF THE DRAWINGS

Exemplary non-limiting embodiments of the invention described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EXEMPLARY EMBODIMENTS

Overview

Figure 1A:
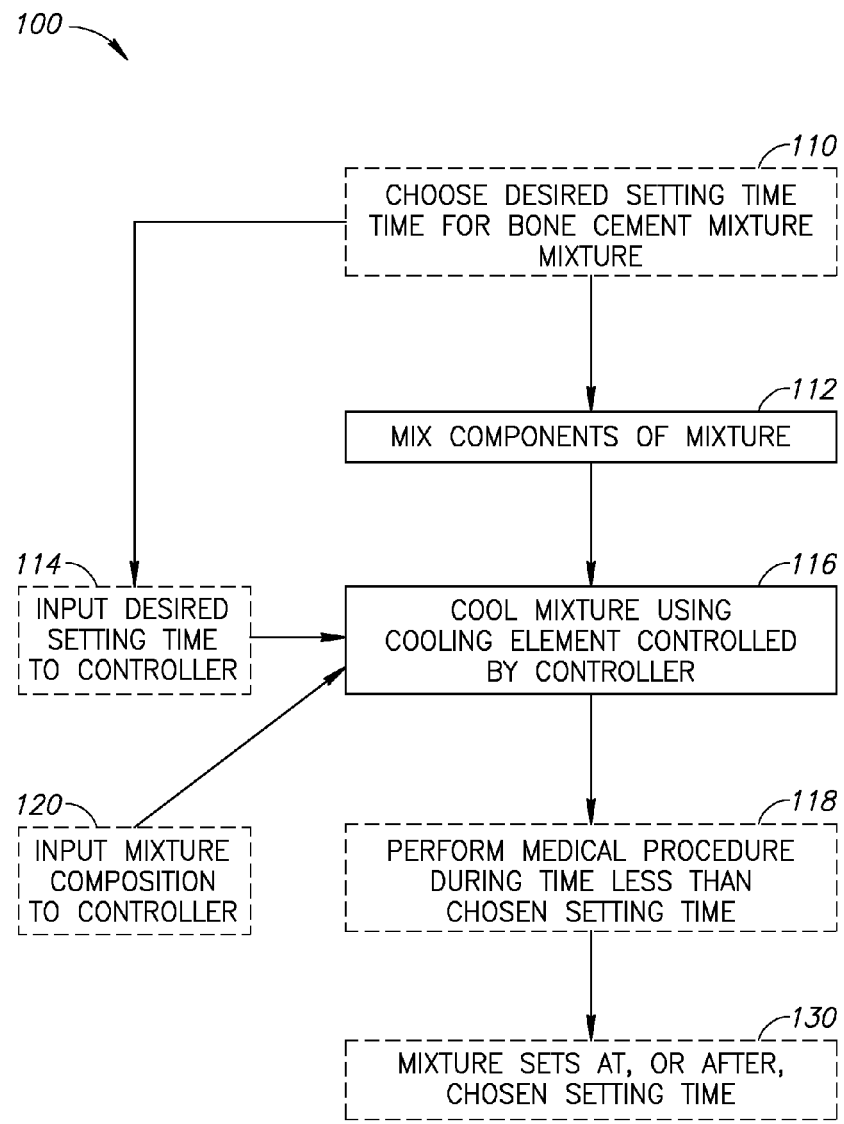
FIG. 1A is a simplified flow diagram illustrating an exemplary method according to some embodiments of the invention.

FIG. 1A illustrates an exemplary method 100 according to an exemplary embodiment of the invention.

Figure 1B:
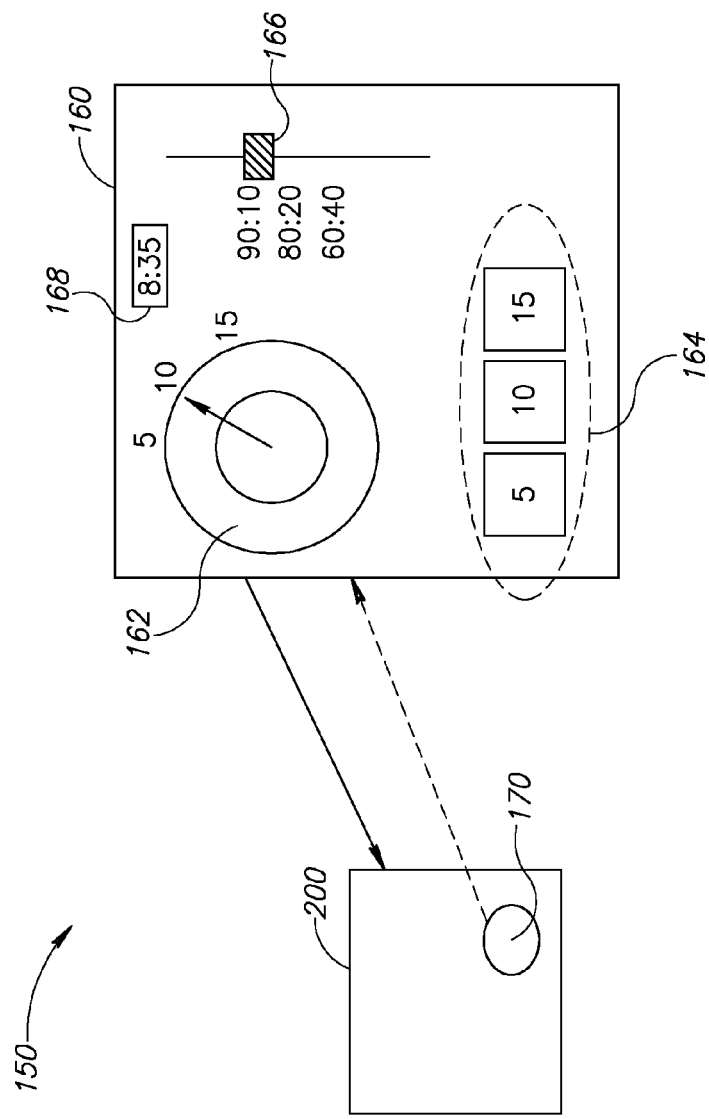
FIG. 1B is a schematic representation of a setting time control system for a reaction mixture according to an exemplary embodiment of the invention.

FIG. 1B schematically depicts an exemplary setting time control system 150 for a reaction mixture according to an exemplary embodiment of the invention.

During use, bone filler material components are typically mixed in an operating theater and used shortly after mixing is complete. In an exemplary embodiment of the invention, a mixing apparatus, cooling system and cement injection system are all provided as sterile objects so that the cement can be mixed and injected in a sterile field established around a site of entry into the body.

Referring now to FIGS. 1A and 1B, at 110 a desired setting time for a bone filler material mixture is optionally chosen. The desired setting time can be chosen 110 in consideration of a particular medical procedure being contemplated. In those embodiments of the invention in which the time is chosen in consideration of a particular medical procedure, the chosen time can be described as an assured minimum working time.

Optionally, the chosen time is defined as a time between setting to a desired minimum viscosity and complete setting. In an exemplary embodiment of the invention, cooling begins only after the minimum viscosity is achieved. Optionally, viscosity is monitored by a viscometer and/or subjectively by a person preparing the mixture. According to various preferred embodiments of the invention an assured minimum working time of, for example, at least 5, at least 10, at least 15 minutes or intermediate values can be the chosen time.

Optionally, a warning timer is provided. The warning timer can be integrated into an existing piece of equipment (e.g. cooling system or injection tool) or be provided as a separate item. Optionally, the warning timer is equipped with a magnet so that it can be affixed to a steel cart or operating table. According to various exemplary embodiments of the invention, the warning timer may signal a beginning or an end of the assured minimum working time. Optionally, the signal is provided a fixed amount of time before the beginning or the end of the assured minimum working time (e.g. 0.5; 1 or 2 minutes or intermediate or greater times). According to various exemplary embodiments of the invention, the warning signal includes a visible signal (e.g. light) and/or an audible signal (e.g. tone, bell or simulated speech).

Components of the mixture are mixed 112 to form a reaction mixture 3. Optionally, mixing 112 occurs in a reservoir 1.

The chosen time is optionally input 114 into a controller 160. Input 114 may be, for example, by means of a continuous scale input device (e.g. calibrated knob 162) or a discrete step input device (e.g. buttons 164). In an exemplary embodiment of the invention, the input device for the chosen time is marked in units of time (e.g. minutes or seconds). In an exemplary embodiment of the invention, the controller controls a cooling mechanism 200 which cools 116 the mixture after and/or during mixing.

Optionally, data pertaining to composition of the mixture is also input 120 to controller 160. Input of data pertaining to mixture composition can be, for example, via calibrated sliding bar 166. Optionally, the mixture is defined in terms of one or more of polymer/monomer ratio, chemical composition and physical characteristics of at least one component of the mixture. Optionally, physical characteristics of mixture components such a particle size and/or average molecular weight influence reaction kinetics. In an exemplary embodiment of the invention, a cooling program implemented by controller 160 is based upon both mixture composition and chosen setting time.

In some exemplary embodiments of the invention, data pertaining to a volume of the mixture is also input.

In some exemplary embodiments of the invention a cooling system is provided for a mixture of a defined volume. Optionally, the cooling system sends a signal to controller 160 indicating a mixture volume and controller 160 implements a cooling program in accord with the signal.

A medical procedure can then be performed 118 during an amount of time less than the chosen setting time. In an exemplary embodiment of the invention, mixture 3 sets 130 at, optionally after, the chosen setting time.

In some exemplary embodiments of the invention control (solid arrow in FIG. 1B) of cooling system 200 by controller 160 is modified by feedback (dotted arrow) from a sensor 170. Sensor 170 is optionally deployed in the mixture or in a wall of a container containing the mixture.

Optionally, controller 160 is equipped with a time display 168. According to various exemplary embodiments of the invention, display 168 can indicate elapsed and/or remaining time. Optionally, the warning timer is incorporated into time display 168.

In some exemplary embodiments of the invention, controller 160 includes circuitry capable of controlling cooling based upon calculation and/or feedback from a sensor in the cooling system.

Exemplary Cooling Mechanism Configurations

Figure 2:
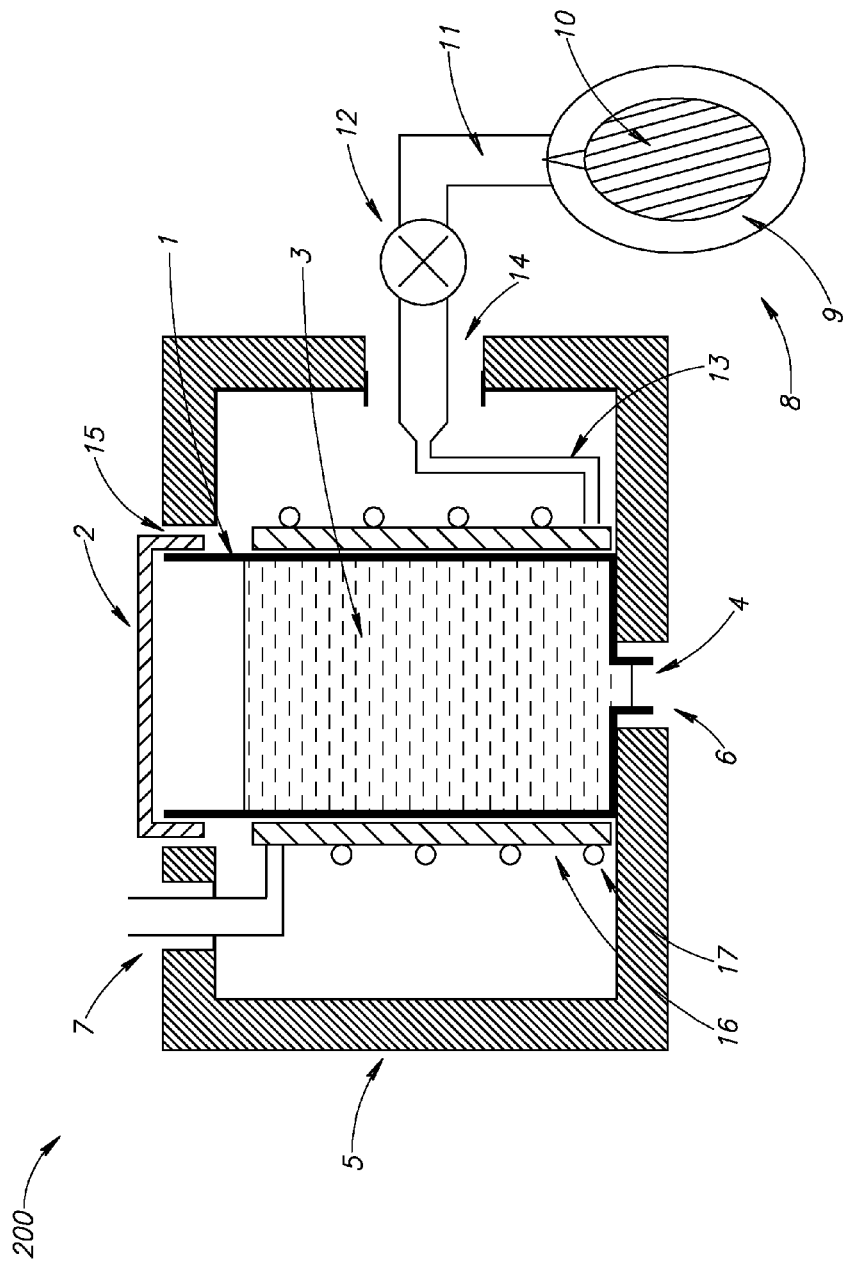
FIG. 2 is a lateral cross sectional view of a cooling mechanism according to an exemplary embodiment of the invention.
Figure 3:
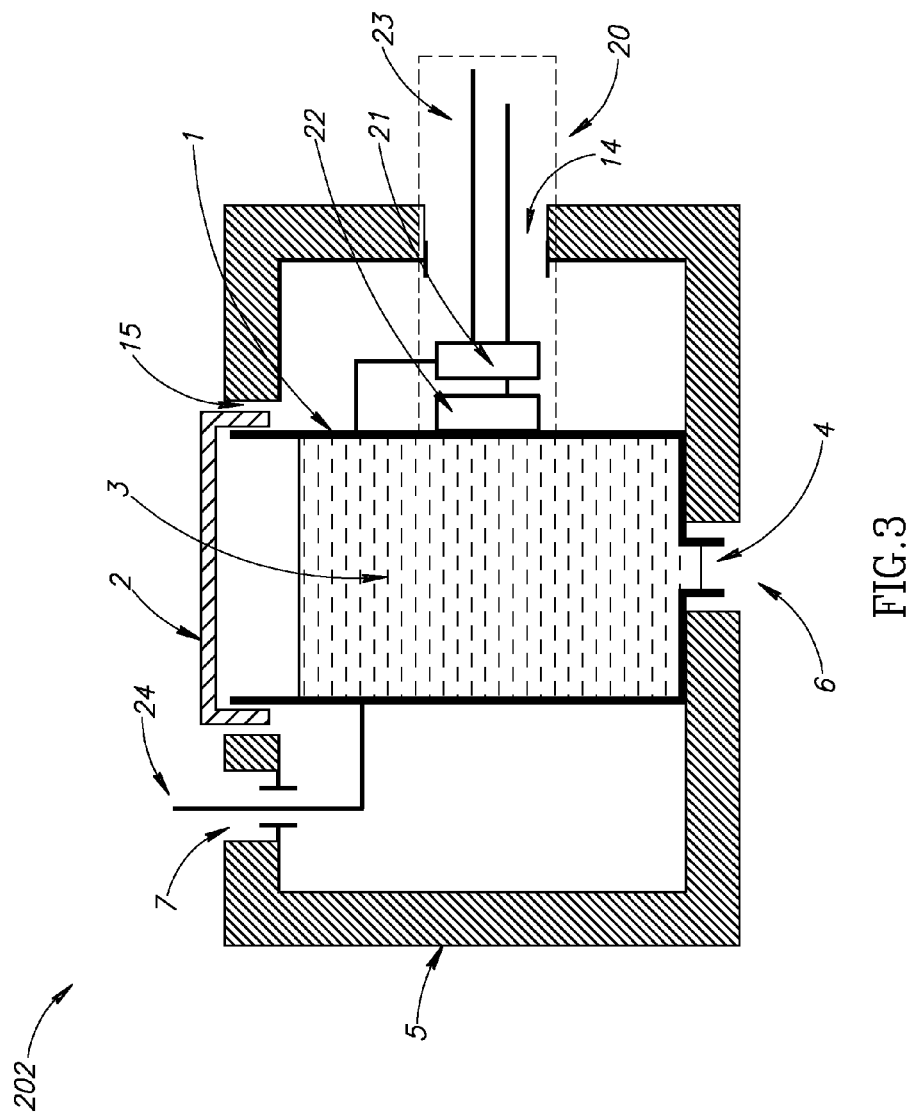
FIG. 3 is a lateral cross sectional view of a cooling mechanism according to another exemplary embodiment of the invention.
Figure 4:
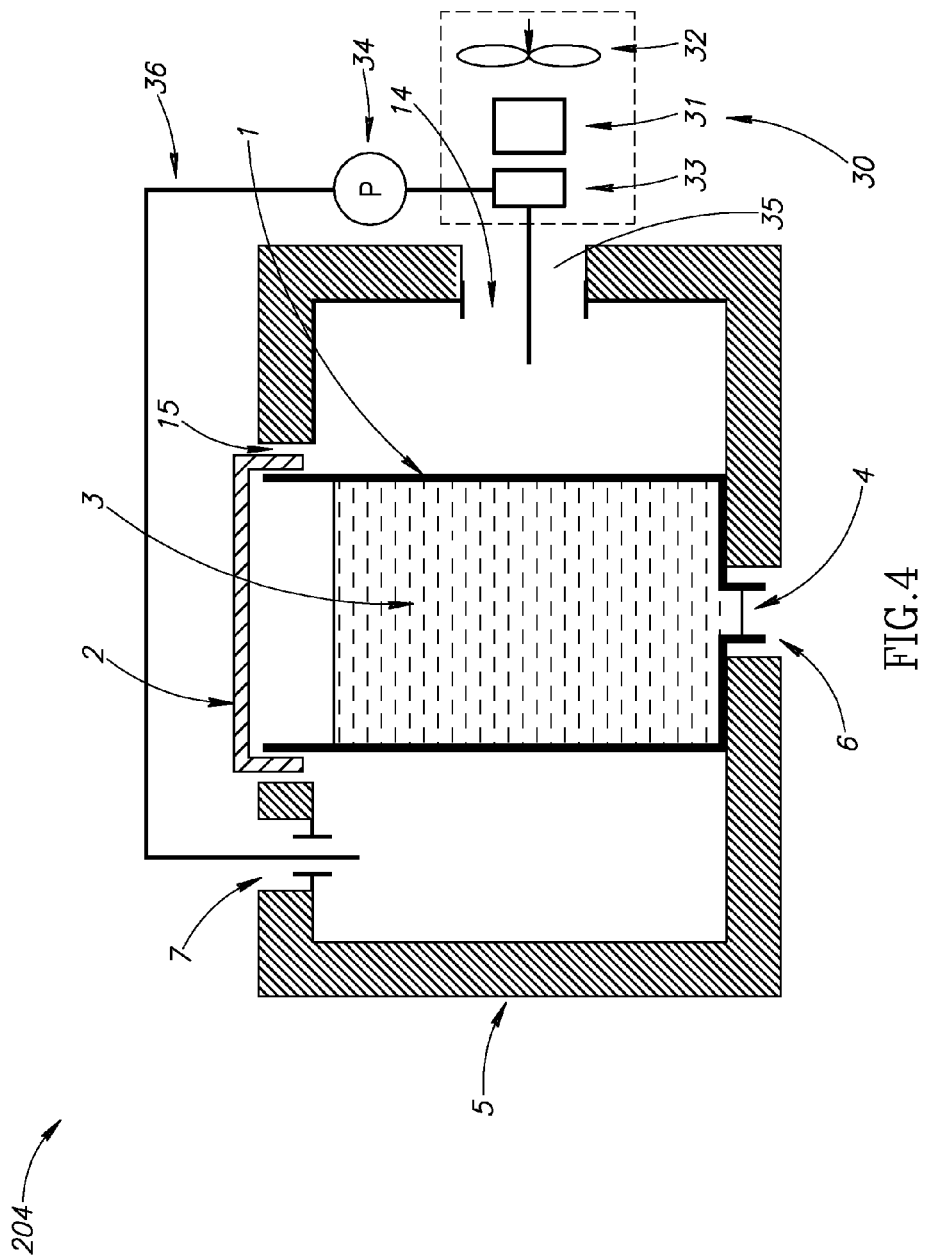
FIG. 4 is a lateral cross sectional view of a cooling mechanism according to yet another exemplary embodiment of the invention.

FIGS. 2, 3 and 4 illustrate different exemplary cooling mechanisms according to various embodiments of the invention. Each depicted system is characterized by a different type of cooling unit, although all are suitable for use in performance of method 100 as described above. FIG. 2 illustrates a system 200 based upon fixed cylinder gas-expansion. FIG. 3 illustrates a system 202 based upon direct Peltier thermoelectric cooling. FIG. 4 illustrates a system 204 based upon an outer thermoelectric heat exchange unit. Other cooling technologies known to those of ordinary skill in the art can be substituted for the depicted cooling mechanisms which are exemplary only.

FIG. 2 is a lateral cross-sectional view of a cooling mechanism 200. In the depicted embodiment, system 200 includes a reservoir 1 adapted to hold a polymerization mixture 3 (e.g. bone filler material or bone cement). Reservoir 1 is optionally at least partially surrounded by a thermal insulation chamber 5. In the depicted embodiment an evaporative cooling unit 8 cools mixture 3.

Evaporative cooling unit 8 includes a cooling fluid chamber 9 containing a cooling fluid 10. Fluid chamber 9 is connected to cooling line 11. Cooling fluid 10 can flow through line 11 into insulation chamber 5, for example via opening 14. Cooling line 11 is optionally equipped with a control valve 12 and/or a portion 13 characterized by a narrow inner diameter (e.g. capillary tube). These optional features can regulate a flow of cooling fluid 10 through line 11 to chamber 5 so that a desired degree of cooling of mixture 3 is achieved. In an exemplary embodiment of the invention, the desired degree of cooling provides the chosen setting time for mixture 3.

In some exemplary embodiments of the invention, evaporative cooling unit 8 includes a pressurized gas cylinder serving as fluid chamber 9 and a regulator serving as valve 12.

In other exemplary embodiments of the invention evaporative cooling unit 8 includes, a compressor which compresses $N_2$ and/or $O_2$ gas from a wall port in lieu of cooling fluid chamber 9. These embodiments of the invention may be convenient to implement in operating theaters equipped with $N_2$ and/or $O_2$ gas ports. Optionally, the compressor is electrically powered. In an exemplary embodiment of the invention, the compressor is connectable to a standard electrical wall outlet.

FIG. 2 depicts an optional cooling coil 17 wrapped (e.g. spirally) around reservoir 1. An optional thermally conductive sleeve 16 is also depicted deployed between reservoir 1 and coil 17. In an exemplary embodiment of the invention, cooling fluid 10 flows through line 11 into coil 17. Optionally, a rate of flow of fluid 10 is regulated by valve 12 and/or an inner diameter of tube segment 13. Optionally, sleeve 16 serves to increase an efficiency of heat transfer from an exothermic reaction mixture 3 in reservoir 1 to fluid flowing through coil 17.

In some exemplary embodiments of the invention, gas is employed for convection based cooling. In those exemplary embodiments of the invention which rely upon convection cooling, gas flows through a space between mixing chamber 1 and insulation chamber 5 without being routed through tube 17.

In an exemplary embodiment of the invention, maintaining a low rate of flow of cooling fluid 10 through line 11 can contribute to a more efficient heat exchange process and/or contribute to lower working pressures within insulation chamber 5. Low rates of flow are optionally 1, 5, 10, 20, 50, 100, 500 or 1000 ml/minute or lesser or intermediate or greater values. Actual flow rates employed may vary with system parameters including, but not limited to, type of gas, amount of cooling required and pressure.

In an exemplary embodiment of the invention gas-evaporation cooling (gas expansion cooling if N2 is employed), the gas expand/evaporates as it enters insulation chamber 5 from narrow tube 13. The expansion/evaporation causes the gas to cool. Cooled gas escapes from opening 7. Optionally, valve 12 maintains a high pressure upstream and a low pressure downstream to insure that cooling occurs in insulation chamber 5.

In evaporation or convection based cooling, cooling fluid 10 flows through connection line 11 and exits narrow section 13 into insulation chamber 5 where fluid 10 is dispersed in the space around reservoir 1 and warmed by heat emanating from walls of reservoir 1. Optionally, dispersal is via a planned flow course (not shown). Warmed cooling fluid 10 can then exit insulation chamber 5 through opening 7. Exit may optionally be due to pressure within chamber 5 caused by flow from line 11 and/or due to a tendency of warmer gases to rise.

In some exemplary embodiments of the invention, reservoir 1 serves also as a mixing chamber where components of reaction mixture 3 are mixed prior to and/or during cooling. According to these embodiments of the invention, a mixing mechanism (not pictured) can be introduced into reservoir 1, for example by removing cover 2. Optionally, cooling during mixing retards development of exothermic reaction conditions from an early stage and contributes to a long setting time.

Cooling systems according to various exemplary embodiments of the invention (e.g. embodiments depicted in FIGS. 2, 3 and 4) are capable of cooling a mixture and retarding reaction kinetics during mixing and/or after mixing and/or during injection.

In an exemplary embodiment of the invention, reservoir 1 is adapted for connection to a material delivery system. As depicted in FIG. 2, reservoir 1 optionally includes two openings: a first opening depicted closed by cover 2 and a second opening 4. Optionally, opening 4 can serve as a delivery port and is adapted for connection to a bone access needle and/or an injection tube/cannula. Optionally, the opening depicted closed by cover 2 is adapted for attachment to an actuator, e.g. a hydraulic actuator. In an exemplary embodiment of the invention, the actuator exerts sufficient force on reaction mixture 3 to drive the mixture out of reservoir 1 via opening 4 and a needle or cannula attached thereto.

In the depicted embodiment, insulation chamber 5 includes an upper opening 15 so that reservoir 1 can receive a mixing element and/or connect to an actuator while seated in chamber 5. In the depicted embodiment, insulation chamber 5 includes a lower opening 6 so that opening 4 of reservoir 1 can be connected to a needle and/or cannula while seated in chamber 5. Optionally, opening 15 is elastic so it can change its diameter to fit various items mounted thereupon, Cooling systems according to various exemplary embodiments of the invention (e.g. embodiments depicted in FIGS. 2, 3 and 4) are adapted to connect to mixers of the type described in co-pending U.S. application Ser. No. 11/428,908 entitled "Mixing Apparatus" which is fully incorporated herein by reference.

In an exemplary embodiment of the invention, thermal insulation chamber 5 at least partially thermally isolates reservoir 1 from an ambient environment. In those exemplary embodiments of the invention which do not employ a cooling coil 17, there is optionally an empty space between an outer wall of reservoir 1 and an inner surface of insulation chamber 5. The empty space is filled by cooling fluid 10 during cooling.

In an exemplary embodiment of the invention, increasing a portion of an outer surface of reservoir 1 in contact with the space contributes to more efficient cooling of mixture 3 in reservoir 1. According to various exemplary embodiments of the invention, 50, 60, 70, 80 or 90% or intermediate or greater percentages of an outer surface of reservoir 1 is in contact with the space.

Additionally or alternatively, decreasing a total volume of the space contributes to more efficient cooling of mixture 3 in reservoir 1. According to various exemplary embodiments of the invention, the space has a volume of 5, 10, 20 or 50 ml or lesser or greater or intermediate volumes.

According to various embodiments of the invention, insulation chamber 5 may be provided with openings adapted for different purposes. In FIG. 2, four optional openings in chamber 5 are depicted. Opening 14 facilitates entrance of cooling fluid line 11, opening 15 is adapted to accommodate cover 2, opening 7 serves as an exhaust port for warmed cooling gas and opening 6 provides access to exit port 4 of reservoir 1 so that a needle or cannula can be connected thereto. Optionally, larger or smaller numbers of openings are present in various exemplary embodiments of the invention.

According to various exemplary embodiments of the invention, cooling fluid chamber 9 is constructed of different materials, and with different geometries adapted to contain pressurized fluids and/or gases.

Exemplary cooling fluids include, but are not limited to: He, H2, Ne, O2, F2, $N_2$, $NF_3$, CO, A, $SiH_4$, $CF_4$, $C_2H_6$, $CH_4$, $CF_3Cl$, $C_2H_4$, $B_2H_6$, NO, $CHF_3$, $CHF_2Cl$, $C_2F_3Cl$, Kr, $CF_2Cl_2$, $C_2F_4$, CHFCl, $C_2F_2Cl_2$, $SF_4$, HCl, Xe, $CFCl_3$, $Cl_2$, $C_2F_6$, $CH_3Cl$, $CH_2Cl_2$, $CO_2$ [taken from Scot, B. R. (1963), "Cryogenic Engineering", Met-Chem Research Inc., Colorado 80307; the contents of which are fully incorporated herein by reference].

In those exemplary embodiments of the invention where an inert non-toxic cooling is employed, opening 7 is optionally vented to the operating theatre.

In other exemplary embodiments of the invention, opening 7 is optionally vented to a trap or fume hood or to outside air.

FIG. 3 is a lateral cross-sectional view of an additional exemplary cooling mechanism 202 including a thermoelectric cooling unit. Other portions of the system are similar to the embodiment depicted in FIG. 2. Optionally, sleeve 16 (not pictured) is included. As schematically illustrated, system 202 may include one or more Peltier Effect elements 20 (a single element 20 is pictured for clarity) comprising a cooling side 22 and a heating side 21 (n-type and p-type) connected to each other at two junctions (Peltier junctions). When a current is passed by wires 23, through the Peltier element the current drives a transfer of heat from one junction to the other: junction 22 cools off while junction 21 heats up. In the depicted embodiment, heat emanating from reaction mixture 3 is absorbed by cooling side 22, while the heat generated by heating side 21 is expelled through opening 14.

The depicted configuration is configured to provide a modest degree of cooling. According to various exemplary embodiments of the invention, a degree of cooling supplied by Peltier cooling unit 20 is increased by one or more of the following: providing multiple Peltier units 20, placing cooling side 22 in direct contact with mixture 3, positioning heating side 21 outside of opening 14, configuring heating side 21 with a large surface area and cooling heating side 21 (e.g. with a fan). Optionally, an external cable 24 is provided to connect to an electric socket. In some exemplary embodiments of the invention, a portion, optionally all of, insulation chamber 5 is removed. Optionally, removal of some or all of chamber 5 permits heat from mixture 3 to dissipate through walls of reservoir 1.

FIG. 4 is a lateral cross-sectional view of another additional exemplary cooling mechanism 204 which incorporates an outer thermoelectric cooling unit 30. Other portions of the system are similar to the embodiment depicted in FIG. 2. In the schematically depicted embodiment, cooling unit 30 includes a cooling element 31 (e.g., a Peltier Effect element; pictured here as a single unit for clarity). Optionally, cooling unit 30 includes fan 32. In an exemplary embodiment of the invention, fan 32 is adapted to cool a heated side of cooling element 31. As schematically illustrated, heat exchanger 33 may be connected to tubing 36 which serves to transfer a fluid in a closed loop with insulation chamber 5, by using a pump 34. The cooling fluid is cooled down by heat exchanger 33 and then flowed into insulation chamber 5, where it absorbs the heat generated by reaction mixture 3. The heated fluid then flows through opening 7 back into tubing 36 where it is recycled to heat exchanger 33 for cooling.

Although bone filler material mixtures typically polymerize in an exothermic reaction, principles of the invention can also be employed to generate heat. In particular, the Peltier elements of exemplary embodiments depicted in FIGS. 2 and 4 can be used for heating by reversing the current flow. Optionally, this heat generating capacity is used to moderate a general cooling effect, for example in response to feedback from sensor 170 and/or to speed up reaction kinetics, for example, to reduce waiting time until a desired minimum viscosity is achieved.

Incorporation into an Exemplary Bone Filler Material Injection System

Figure 5:
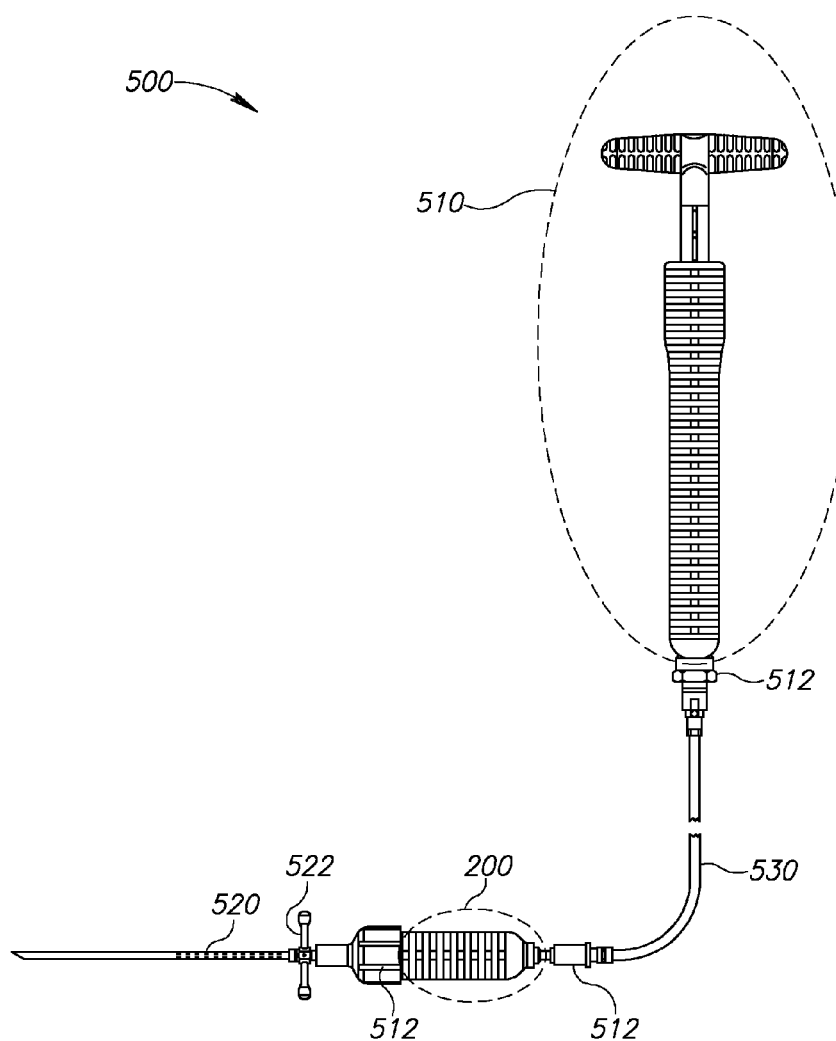
FIG. 5 depicts incorporation of an exemplary cooling mechanism according to an embodiment of the invention into a bone filler material injection system.

FIG. 5 illustrates incorporation of an exemplary cooling system 200 according to an embodiment of the invention into an exemplary bone filler material injection system 500 of a type described in WO 2006/090379, the disclosure of which is fully incorporated herein by reference. The depicted system, and the cooling systems described here, are well suited to use with bone cements characterized by a rapid transition to high viscosity after mixing as described in co-pending U.S. application Ser. No. 11/461,072 entitled "Bone Cement and Methods of Use Thereof" which is fully incorporated herein by reference.

Briefly, bone filler material injection system 500 comprises a hydraulic mechanism 510 which applies pressure to a hydraulic fluid in tube 530 in fluid communication with reaction mixture 3 contained in reservoir 1 of cooling system 200 shown schematically as a dotted region, in FIG. 5 an illustrated in greater detail in FIG. 2. Mixture 3 is forced out of cannula 520 (optionally any needle or tube) and into a desired injection site.

In some exemplary embodiments of the invention, cooling system 200 installed as part of injection system 500 continues to cool mixture 300 during the injection process.

In other exemplary embodiments of the invention, cooling system 200 pre-cools mixture 300 and cooling does not continue during the injection process.

Optionally, a degree of cooling is sufficient to counteract body heat applied to mixture 3 flowing through cannula 520 to a significant degree. Alternatively or additionally, the cement is injected at a temperature which is not sufficiently cold to cool surrounding tissue to any significant degree. In an exemplary embodiment of the invention, injection of cooled cement prevents or retards heating of surrounding tissue as the reaction continues to completion inside the body.

In the depicted embodiment of system 500, optional connectors 512 are visible connection portions of the system. Connectors 512 can be, for example threaded connectors, Luer lock connectors, snap to fit connectors or any other connectors which can withstand the pressure supplied by hydraulic mechanism 510. In the depicted embodiment, cannula 520 is fitted with a handle 522. Optionally, handle 522 contributes to ease of connection between cannula 520 and connector 512 of cooling system 200. Optionally, handle 522 provides insulation so that fingers are not chilled during attachment of cannula 520 to connector 512 of cooling system 200.

In other exemplary embodiments of the invention, cooling systems 202 or 204 (or other types of cooling systems) are substituted for cooling system 200 in bone filler material injection system 500.

Bone filler material injection system 500 is exemplary only and cooling systems according to various embodiments of the invention can be advantageously employed in any available injection system. One of ordinary skill in the art will be able to select an available injection system and adapt the shape of a cooling system according to an exemplary embodiment of the invention to conform to the selected injection system.

Construction Considerations

In an exemplary embodiment of the invention, reservoirs 1 and/or 5 are constructed of lightweight plastics, optionally nylon. Optionally, materials with a high heat transfer capacity are selected. In an exemplary embodiment of the invention, reservoirs 1 and/or 5 are re-usable. Optionally, re-usable parts are sterilize-able. Sterilization can be performed, for example, using steam pressure and/or UV irradiation.

In an exemplary embodiment of the invention, cooling fluid chamber 9 contains sufficient cooling fluid 10 to cool mixture 3 for 5, 10, 15 or 20 minutes or lesser or intermediate or greater times. Typically, mixture 3 will have a volume of 5 to 20 ml, optionally about 10 to 12 ml. In some cases, larger volumes of mixture 3 are prepared, for example when several vertebra are being repaired in a single procedure.

In an exemplary embodiment of the invention, a portion of cooling fluid 10 is used to pre-cool sleeve 16. Pre-cooling can render sleeve 16 a thermal mass. Optionally, use of a thermal mass contributes to an increase in predictability.

Optionally, 2, 5, 10, 15, 20, 50, 100, 200, 500, or 1000 grams or lesser or intermediate or greater amounts of cooling fluid 10 are provided in chamber 9. In an exemplary embodiment of the invention, chamber 9 is connected to chamber 5 by a flexible tubing 11. Optionally, chamber 9 can be installed at a distance from other portions of system 200. In those embodiments of the invention where chamber 9 is installed at a distance, fluid line 11 is elongated. Optionally, an elongated fluid line 11 can be insulated to prevent loss of cooling capacity en-route. An exact amount of cooling fluid 10 supplied in chamber 11 can vary with one or more of an amount of heat generated by mixture 3, a specific fluid 10 employed and a desired degree by which reaction kinetics are to be retarded. In an exemplary embodiment of the invention, installation of chamber 9 at a distance contributes to a perceived weight reduction in the cooling system for a user. The phrase "at a distance" as used here refers to any distance which permits a user to manipulate other portions of system 200 without moving chamber 9. In various exemplary embodiments of the invention, at a distance can refer to 0.2, 0.3, 0.5, 1, 2, 5, 10, 50 or 100 meters or lesser or greater or intermediate distances. Larger distance are typical of embodiments where a cooling gas is supplied from a wall valve connected to a gas distribution system with large gas cylinders stored in a central location. Gas distribution systems of this type are common in hospitals, especially for $O_2$.

In those exemplary embodiments of the invention which rely upon electric power for cooling (e.g. system 202 of FIG. 3 and system 204 of FIG. 4), power can be supplied by an external source (e.g. wall outlet) or internal source (e.g. battery). In those exemplary embodiments of the invention which employ an external power source, a step down transformer (e.g. 110V to 9V or 220V to 9V) can optionally be employed. In those exemplary embodiments of the invention which employ an internal power source, one or more standard batteries (e.g. watch battery; AAA cell; AA cell; C cell; D cell or 9V) can be employed to provide electric power. An exact amount of electric power consumed by the cooling system can vary with one or more of an amount of heat generated by mixture 3, an amount of time during which the system operates and a desired degree by which reaction kinetics are to be retarded.

In an exemplary embodiment of the invention, controller 160 relies upon execution of various commands and analysis and translation of various data inputs. Any of these commands, analyses or translations may be accomplished by software, hardware or firmware according to various embodiments of the invention. In an exemplary embodiment of the invention, machine readable media contain instructions for a cooling program based upon a chosen setting time of a reaction mixture, optionally a polymerization reaction mixture, optionally an acrylic polymerization reaction mixture are provided. In an exemplary embodiment of the invention, controller 160 executes instructions for a cooling program based upon a chosen setting time of a reaction mixture. Optionally, the instructions are subject to modification based upon feedback from a temperature and/or a viscosity sensor 170 in reaction mixture 3 and/or reservoir 1. In some embodiments of the invention, cooling is uniform (e.g. to a constant temperature or removing a fixed amount of energy per unit time). In other embodiments of the invention, the cooling program is non-uniform and provides greater energy removal when reaction kinetics cause the most heating.

In an exemplary embodiment of the invention, controller 160 receives input regarding a composition and/or volume of mixture 3 from machine readable data provided with components of the mixture (e.g. on labels or as part of packaging. The machine readable data can be provided, for example, as a bar code or on an RFID tag or on a smart chip. According to these embodiments of the invention, controller 160 is equipped with or connectable to a reader compatible with a format of the machine readable data. Optionally, controller sets all parameters except for the chosen time based upon the machine readable data.

Factory Calibration

In some exemplary embodiments of the invention, control of a setting time is less exact and/or in not apparent to a user. In some cases, it is sufficient to know that a setting time of a bone filler material mixture is extended by cooling. Optionally, a cooling system (e.g. of a type depicted in one of FIG. 2, 3 or 4) adapted for use with a mixer and/or injection system 500 is supplied with no apparent calibration indicator.

In an exemplary embodiment of the invention, the cooling system is manufactured with a cooling capacity which is sufficient for an intended amount of filler material of a specific type. From the standpoint of the user, only an ON/OFF switch is apparent. However the cooling capacity of the cooling system is sufficient to extend a setting time of a typical reaction mixture to a time determined by the manufacturer. In an exemplary embodiment of the invention, components of the filler material mixture are provided together with the cooling system and/or a mixer and/or injection system 500 as a kit.

For example, a kit may be supplied with components of a mixture 3 with a nominal setting time of 10 minutes when prepared without cooling. Use of a cooling system provided as part of the kit can extend the setting time to 20 minutes. Optionally, the kit itself is labeled as "20 minute assured working time" cement kit.

The present invention has been described using detailed descriptions of embodiments thereof that are provided by way of example and are not intended to necessarily limit the scope of the invention. In particular, numerical values may be higher or lower than ranges of numbers set forth above and still be within the scope of the invention. The described embodiments comprise different features, not all of which are required in all embodiments of the invention. Some embodiments of the invention utilize only some of the features or possible combinations of the features. Alternatively or additionally, portions of the invention described/depicted as a single unit may reside in two or more separate physical entities which act in concert to perform the described/depicted function. Alternatively or additionally, portions of the invention described/depicted as two or more separate physical entities may be integrated into a single physical entity to perform the described/depicted function. Variations of embodiments of the present invention that are described and embodiments of the present invention comprising different combinations of features noted in the described embodiments can be combined in all possible combinations including, but not limited to use of features described in the context of one embodiment in the context of any other embodiment. The scope of the invention is limited only by the following claims.

In the description and claims of the present application, each of the verbs "comprise", "include" and "have" as well as any conjugates thereof, are used to indicate that the object or objects of the verb are not necessarily a complete listing of members, components, elements or parts of the subject or subjects of the verb.

All publications and/or patents and/or product descriptions cited in this document are fully incorporated herein by reference to the same extent as if each had been individually incorporated herein by reference.

The invention claimed is:

1. Apparatus for regulating setting time of a bone filler material mixture in a bone filler material injection system, the apparatus comprising:
   (a) a reservoir in the bone filler material injection system;
   (b) a cooling mechanism adapted to cool a bone filler material mixture in the reservoir as a portion of the mixture is injected into a patient; and
   (c) control circuitry adapted to output a control signal to the cooling mechanism so that the mixture does not set before a minimum setting time.

2. Apparatus according to claim 1, wherein the control circuitry is adapted to receive a data input pertaining to a minimum setting time.

3. Apparatus according to claim 1, comprising:
   (d) a data input device calibrated so that a user can select a minimum setting time.

4. Apparatus according to claim 3, comprising wherein the data input device is calibrated with a continuous time scale.

5. Apparatus according to claim 3, comprising wherein the data input device is calibrated in a scale having discrete steps of time.

6. Apparatus according to claim 1, comprising:
   (d) a data input device adapted for input of data pertaining to the mixture.

7. Apparatus according to claim 6, wherein the data pertains to a ratio of components of the mixture.

8. Apparatus according to claim 6, wherein the data pertains to a volume of the mixture.

9. Apparatus according to claim 6, wherein the data pertains a chemical composition of the mixture.

10. Apparatus according to claim 6, wherein the data pertains to physical characteristics of at least one component of the mixture.

11. Apparatus according to claim 1, comprising:
    (d) a sensor adapted to detect a temperature of the mixture and transmit data pertaining to the temperature to the controller.

12. Apparatus according to claim 11, wherein the control circuitry modifies the control signal responsive to the data pertaining to the temperature.

13. Apparatus according to claim 1, comprising:
    (d) a sensor adapted to detect a viscosity of the mixture and transmit data pertaining to the viscosity to the controller.

14. Apparatus according to claim 13, wherein the control circuitry modifies the control signal responsive to the data pertaining to the viscosity.

15. Apparatus according to claim 1, provided as a sterile apparatus.

16. Apparatus for regulating setting time of a bone filler material in a bone filler material injection system, the apparatus comprising:
    (a) a reservoir in the bone filler material injection system coupled to an injection cannula;
    (b) a cooling mechanism adapted to cool a bone filler material in the reservoir as a portion of the bone filler material is forced through the injection cannula; and
    (c) control circuitry adapted to output a control signal to the cooling mechanism so that the bone filler material does not set before a minimum setting time.

17. Apparatus according to claim 16, wherein the cooling mechanism comprises a thermoelectric cooling mechanism.

18. Apparatus for regulating setting time of a bone filler material in a bone filler material injection system, the apparatus comprising:
    (a) a reservoir in the bone filler material injection system, the reservoir having a first end and a second end, the first end being coupled to a hydraulic actuator;
    (b) a cooling mechanism adapted to cool a bone filler material in the reservoir; and
    (c) control circuitry adapted to output a control signal to the cooling mechanism so that the bone filler material does not set before a minimum setting time.

19. Apparatus according to claim 18, further comprising an injection cannula coupled to the second end of the reservoir.

20. Apparatus according to claim 19, further comprising a tube extending between the hydraulic actuator and the first end of the reservoir and having hydraulic fluid disposed therein for exerting pressure on the bone filler material.

* * * * *